US012697156B2

(12) United States Patent
Kostrzewski et al.

(10) Patent No.: US 12,697,156 B2
(45) Date of Patent: Aug. 4, 2026

(54) ROBOTIC SURGICAL SYSTEMS AND METHODS FOR ROD BENDING

(71) Applicant: KB MEDICAL SA, Audubon, PA (US)

(72) Inventors: Szymon Kostrzewski, Lausanne (CH); Olivier Chappuis, Lutry (CH)

(73) Assignee: Globus Medical Inc., Audubon, PA (US)

( * ) Notice: Subject to any disclaimer, the term of this patent is extended or adjusted under 35 U.S.C. 154(b) by 40 days.

(21) Appl. No.: 17/538,303

(22) Filed: Nov. 30, 2021

(65) Prior Publication Data

US 2022/0087729 A1      Mar. 24, 2022

Related U.S. Application Data

(63) Continuation of application No. 15/253,065, filed on Aug. 31, 2016, now abandoned.

(Continued)

(51) Int. Cl.
*A61B 17/70*      (2006.01)
*A61B 17/88*      (2006.01)
(Continued)

(52) U.S. Cl.
CPC .......... *A61B 17/8863* (2013.01); *A61B 17/70* (2013.01); *A61B 34/10* (2016.02); *A61B 34/20* (2016.02); *A61B 34/30* (2016.02); *A61B 46/10* (2016.02); *A61B 90/57* (2016.02); *B21D 7/02* (2013.01); *B21D 7/12* (2013.01); *A61B 2017/00876* (2013.01); *A61B 2034/102* (2016.02); *A61B 2034/107* (2016.02); *A61B*

*2034/108* (2016.02); *A61B 46/27* (2016.02); *A61B 2090/066* (2016.02); *A61B 2090/508* (2016.02)

(58) Field of Classification Search
None
See application file for complete search history.

(56) References Cited

U.S. PATENT DOCUMENTS

| | | | |
|---|---|---|---|
| 4,150,293 A | 4/1979 | Franke | |
| 5,246,010 A | 9/1993 | Gazzara et al. | |

(Continued)

FOREIGN PATENT DOCUMENTS

| | | | |
|---|---|---|---|
| JP | 08132140 A | 5/1996 | |
| JP | 2009537230 A | 10/2009 | |

(Continued)

OTHER PUBLICATIONS

Motoman HP20 brochure, Feb. 2007, accessed from http://motion. me.ucsb.edu/ME179P-Winter2023/handouts/MOTOMAN-HP20-brochure.pdf (Year: 2007).*

(Continued)

*Primary Examiner* — Jan Christopher L Merene

(57) ABSTRACT

The disclosed technology relates to a rod bending machine for use with a robotic surgical system in an operating room. The system which is capable to bend rods for surgeries directly in the operating room. The rigidity of the rods is such that the robotic arm alone would have to be huge to provide sufficient forces and torques. This invention introduces bending module integrated into robotic system which allows free bending of rods within limits required for surgeries.

15 Claims, 30 Drawing Sheets

Related U.S. Application Data

(60) Provisional application No. 62/212,550, filed on Aug. 31, 2015.

(51) Int. Cl.

| | |
|---|---|
| *A61B 34/10* | (2016.01) |
| *A61B 34/20* | (2016.01) |
| *A61B 34/30* | (2016.01) |
| *A61B 46/10* | (2016.01) |
| *A61B 90/57* | (2016.01) |
| *B21D 7/02* | (2006.01) |
| *B21D 7/12* | (2006.01) |
| A61B 17/00 | (2006.01) |
| A61B 46/27 | (2016.01) |
| A61B 90/00 | (2016.01) |
| A61B 90/50 | (2016.01) |

(56) References Cited

U.S. PATENT DOCUMENTS

| | | | |
|---|---|---|---|
| 5,598,453 | A | 1/1997 | Baba et al. |
| 5,772,594 | A | 6/1998 | Barrick |
| 5,987,960 | A | 11/1999 | Messner et al. |
| 6,031,888 | A | 2/2000 | Ivan et al. |
| 6,144,875 | A | 11/2000 | Schweikard et al. |
| 6,203,196 | B1 | 3/2001 | Meyer et al. |
| 6,306,126 | B1 | 10/2001 | Montezuma |
| 6,314,311 | B1 | 11/2001 | Williams et al. |
| 6,320,929 | B1 | 11/2001 | Von Der Haar |
| 6,477,400 | B1 | 11/2002 | Barrick |
| 6,484,049 | B1 | 11/2002 | Seeley et al. |
| 6,487,267 | B1 | 11/2002 | Wolter |
| 6,490,475 | B1 | 12/2002 | Seeley et al. |
| 6,501,981 | B1 | 12/2002 | Schweikard et al. |
| 6,535,756 | B1 | 3/2003 | Simon et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,666,579 | B2 | 12/2003 | Jensen |
| 6,757,068 | B2 | 6/2004 | Foxlin |
| 6,782,287 | B2 | 8/2004 | Grzeszczuk et al. |
| 6,856,826 | B2 | 2/2005 | Seeley et al. |
| 6,856,827 | B2 | 2/2005 | Seeley et al. |
| 6,920,347 | B2 | 7/2005 | Simon et al. |
| 6,922,632 | B2 | 7/2005 | Foxlin |
| 6,988,009 | B2 | 1/2006 | Grimm et al. |
| 6,996,487 | B2 | 2/2006 | Jutras et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,301,648 | B2 | 11/2007 | Foxlin |
| 7,313,430 | B2 | 12/2007 | Urquhart et al. |
| 7,318,805 | B2 | 1/2008 | Schweikard et al. |
| 7,324,623 | B2 | 1/2008 | Heuscher et al. |
| 7,327,865 | B2 | 2/2008 | Fu et al. |
| 7,460,637 | B2 | 12/2008 | Clinthorne et al. |
| 7,493,153 | B2 | 2/2009 | Ahmed et al. |
| 7,505,617 | B2 | 3/2009 | Fu et al. |
| 7,623,902 | B2 | 11/2009 | Pacheco |
| 7,643,862 | B2 | 1/2010 | Schoenefeld |
| 7,661,881 | B2 | 2/2010 | Gregerson et al. |
| 7,683,331 | B2 | 3/2010 | Chang |
| 7,683,332 | B2 | 3/2010 | Chang |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,725,253 | B2 | 5/2010 | Foxlin |
| 7,726,171 | B2 | 6/2010 | Langlotz et al. |
| 7,760,849 | B2 | 7/2010 | Zhang |
| 7,796,728 | B2 | 9/2010 | Bergfjord |
| 7,813,838 | B2 | 10/2010 | Sommer |
| 7,835,778 | B2 | 11/2010 | Foley et al. |
| 7,835,784 | B2 | 11/2010 | Mire et al. |
| 7,840,256 | B2 | 11/2010 | Lakin et al. |
| 7,844,320 | B2 | 11/2010 | Shahidi |
| 7,853,305 | B2 | 12/2010 | Simon et al. |
| 7,853,313 | B2 | 12/2010 | Thompson |
| 7,900,524 | B2 | 3/2011 | Calloway et al. |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 8,019,045 | B2 | 9/2011 | Kato |
| 8,021,310 | B2 | 9/2011 | Sanborn et al. |
| 8,052,688 | B2 | 11/2011 | Wolf, II |
| 8,086,299 | B2 | 12/2011 | Adler et al. |
| 8,098,914 | B2 | 1/2012 | Liao et al. |
| 8,100,950 | B2 | 1/2012 | St. Clair et al. |
| 8,116,430 | B1 | 2/2012 | Shapiro et al. |
| 8,121,249 | B2 | 2/2012 | Wang et al. |
| 8,150,494 | B2 | 4/2012 | Simon et al. |
| 8,208,708 | B2 | 6/2012 | Homan et al. |
| 8,224,024 | B2 | 7/2012 | Foxlin et al. |
| 8,311,611 | B2 | 11/2012 | Csavoy et al. |
| 8,335,557 | B2 | 12/2012 | Maschke |
| 8,358,818 | B2 | 1/2013 | Miga et al. |
| 8,379,791 | B2 | 2/2013 | Forthmann et al. |
| 8,386,019 | B2 | 2/2013 | Camus et al. |
| 8,394,099 | B2 | 3/2013 | Patwardhan |
| 8,462,911 | B2 | 6/2013 | Vesel et al. |
| 8,526,700 | B2 | 9/2013 | Isaacs |
| 8,541,970 | B2 | 9/2013 | Nowlin et al. |
| 8,560,118 | B2 | 10/2013 | Green et al. |
| 8,597,198 | B2 | 12/2013 | Sanborn et al. |
| 8,611,985 | B2 | 12/2013 | Lavallee et al. |
| 8,630,389 | B2 | 1/2014 | Kato |
| 8,634,897 | B2 | 1/2014 | Simon et al. |
| 8,660,635 | B2 | 2/2014 | Simon et al. |
| 8,678,647 | B2 | 3/2014 | Gregerson et al. |
| 8,696,458 | B2 | 4/2014 | Foxlin et al. |
| 8,706,185 | B2 | 4/2014 | Foley et al. |
| 8,727,618 | B2 | 5/2014 | Maschke et al. |
| 8,738,115 | B2 | 5/2014 | Amberg et al. |
| 8,740,882 | B2 | 6/2014 | Jun et al. |
| 8,781,186 | B2 | 7/2014 | Clements et al. |
| 8,781,630 | B2 | 7/2014 | Banks et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,812,077 | B2 | 8/2014 | Dempsey |
| 8,814,793 | B2 | 8/2014 | Brabrand |
| 8,818,105 | B2 | 8/2014 | Myronenko et al. |
| 8,821,511 | B2 | 9/2014 | Von Jako et al. |
| 8,867,703 | B2 | 10/2014 | Shapiro et al. |
| 8,888,821 | B2 | 11/2014 | Rezach et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |

(56) References Cited

U.S. PATENT DOCUMENTS

| | | | |
|---|---|---|---|
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 12/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 2001/0036302 A1 | 11/2001 | Miller | |
| 2004/0076259 A1 | 4/2004 | Jensen et al. | |
| 2006/0142657 A1* | 6/2006 | Quaid | A61B 90/37 |
| | | | 600/424 |
| 2006/0184396 A1 | 8/2006 | Dennis et al. | |
| 2006/0291612 A1 | 12/2006 | Nishide et al. | |
| 2007/0038059 A1 | 2/2007 | Sheffer et al. | |
| 2007/0073133 A1 | 3/2007 | Schoenefeld | |
| 2007/0199361 A1* | 8/2007 | Yogo | B21D 43/105 |
| | | | 72/149 |
| 2008/0004523 A1 | 1/2008 | Jensen | |
| 2008/0010706 A1 | 1/2008 | Moses et al. | |
| 2008/0013809 A1 | 1/2008 | Zhu et al. | |
| 2008/0082109 A1 | 4/2008 | Moll et al. | |
| 2008/0108991 A1 | 5/2008 | von Jako | |
| 2008/0144906 A1 | 6/2008 | Allred et al. | |
| 2008/0161680 A1 | 7/2008 | Von Jako et al. | |
| 2008/0235052 A1 | 9/2008 | Node-Langlois et al. | |
| 2008/0269596 A1 | 10/2008 | Revie et al. | |
| 2008/0287781 A1 | 11/2008 | Revie et al. | |
| 2008/0300477 A1 | 12/2008 | Lloyd et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0185655 A1 | 7/2009 | Koken et al. | |
| 2009/0198121 A1 | 8/2009 | Hoheisel | |
| 2010/0022874 A1 | 1/2010 | Wang et al. | |
| 2010/0039506 A1 | 2/2010 | Sarvestani et al. | |
| 2010/0125286 A1 | 5/2010 | Wang et al. | |
| 2010/0218580 A1* | 9/2010 | Tomizawa | B21D 7/16 |
| | | | 72/342.94 |
| 2010/0228117 A1 | 9/2010 | Hartmann | |
| 2010/0274120 A1 | 10/2010 | Heuscher | |
| 2010/0275668 A1 | 11/2010 | Riemeier et al. | |
| 2010/0307214 A1* | 12/2010 | Yogo | B21D 43/003 |
| | | | 72/319 |
| 2011/0098553 A1 | 4/2011 | Robbins et al. | |
| 2011/0282189 A1 | 11/2011 | Graumann | |
| 2011/0286573 A1 | 11/2011 | Schretter et al. | |
| 2011/0306873 A1* | 12/2011 | Shenai | A61B 8/0841 |
| | | | 600/424 |
| 2012/0035507 A1 | 2/2012 | George et al. | |
| 2012/0051498 A1 | 3/2012 | Koishi | |
| 2012/0143084 A1 | 6/2012 | Shoham | |
| 2012/0186411 A1 | 7/2012 | Lodahl et al. | |
| 2012/0226145 A1 | 9/2012 | Chang et al. | |
| 2012/0235909 A1 | 9/2012 | Birkenbach et al. | |
| 2012/0294498 A1 | 11/2012 | Popovic | |
| 2013/0016889 A1 | 1/2013 | Myronenko et al. | |
| 2013/0060146 A1 | 3/2013 | Yang et al. | |
| 2013/0094742 A1 | 4/2013 | Feilkas | |
| 2013/0113791 A1 | 5/2013 | Isaacs et al. | |
| 2013/0165937 A1 | 6/2013 | Patwardhan | |
| 2013/0281821 A1 | 10/2013 | Liu et al. | |
| 2013/0307955 A1 | 11/2013 | Deitz et al. | |
| 2013/0342578 A1 | 12/2013 | Isaacs | |
| 2013/0345757 A1 | 12/2013 | Stad | |
| 2014/0046132 A1 | 2/2014 | Hoeg et al. | |
| 2014/0049629 A1 | 2/2014 | Siewerdsen et al. | |
| 2014/0080086 A1 | 3/2014 | Chen | |
| 2014/0096369 A1 | 4/2014 | Matsumoto et al. | |
| 2014/0121676 A1 | 5/2014 | Kostrzewski et al. | |
| 2014/0130810 A1 | 5/2014 | Azizian et al. | |
| 2014/0135796 A1 | 5/2014 | Simon et al. | |
| 2014/0221819 A1 | 8/2014 | Sarment | |
| 2014/0234804 A1 | 8/2014 | Huang et al. | |
| 2014/0371577 A1 | 12/2014 | Maillet et al. | |
| 2015/0039034 A1 | 2/2015 | Frankel et al. | |
| 2015/0085970 A1 | 3/2015 | Bouhnik et al. | |
| 2015/0100091 A1 | 4/2015 | Tohmeh et al. | |
| 2015/0146847 A1 | 5/2015 | Liu | |
| 2015/0150524 A1 | 6/2015 | Yorkston et al. | |
| 2015/0196261 A1 | 7/2015 | Funk | |
| 2015/0213633 A1 | 7/2015 | Chang et al. | |
| 2015/0320471 A1* | 11/2015 | Crawford | B21D 43/006 |
| | | | 72/11.1 |
| 2015/0335480 A1 | 11/2015 | Alvarez et al. | |
| 2015/0342647 A1 | 12/2015 | Frankel et al. | |
| 2016/0005194 A1 | 1/2016 | Schretter et al. | |
| 2016/0166329 A1 | 6/2016 | Langan et al. | |
| 2016/0235480 A1* | 8/2016 | Scholl | A61B 17/7083 |
| 2016/0249990 A1 | 9/2016 | Glozman et al. | |
| 2016/0263646 A1* | 9/2016 | Shazly | B21D 7/02 |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0202629 A1 | 7/2017 | Maillet et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0231710 A1 | 8/2017 | Scholl et al. | |
| 2017/0258426 A1 | 9/2017 | Risher-Kelly et al. | |
| 2017/0273748 A1 | 9/2017 | Hourtash et al. | |
| 2017/0296277 A1 | 10/2017 | Hourtash et al. | |
| 2017/0360493 A1 | 12/2017 | Zucher et al. | |

FOREIGN PATENT DOCUMENTS

| | | | |
|---|---|---|---|
| JP | 2013212392 A | 10/2013 | |
| JP | 2016536051 A | 11/2016 | |

OTHER PUBLICATIONS

Eurobots "MOTOMAN HP 20 industrial robot", https://www.youtube.com/watch?v=UZxG_-Xzzv4, published Jun. 20, 2013 (Year: 2013).*

Used Robotstrade "Robot Motoman HP20 NX 100", https://www.youtube.com/watch?v=Nv0OA2zxsb0, published Nov. 23, 2021 (Year: 2021).*

* cited by examiner

CURBS

1300

1302

ROD
FIXATION

BENDING
MODULE

ROBOTIC SURGICAL SYSTEMS AND METHODS FOR ROD BENDING

RELATED APPLICATIONS

This application is a continuation of U.S. patent application Ser. No. 15/253,065, filed on Aug. 31, 2016 (published as U.S. Pat. Pub. No. 2017-0056086), which claims priority to U.S. Provisional Patent Application No. 62/212,550, filed Aug. 31, 2015, titled ROBOTIC SURGICAL SYSTEMS AND METHODS FOR SPINAL ROD BENDING, the contents of all of which are hereby incorporated by reference in their entireties for all purposes.

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeons field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

One of the most popular methods of bone stabilization involves placement of screws in the bone and joining heads of the screws with rods. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures. As shown in the example depicted in FIG. 2, rods can be bent to allow correction of the spine and adapt to positions of the screws head in the vertebrae. Rods are made of resistant materials (e.g. Titanium alloys, Chrome-Cobalt alloys) and require significant force to bend manually. Additionally, it is hard to manually recreate the desired two-dimensional and three-dimensional pattern, such as the bends shown FIG. 3. Further, as shown in FIG. 4, manual bending can lead to undesirable features that decrease the integrity and mechanical strength of the rods. Manual bending involves tools which may create curbs on the rods which decreases their mechanical strength. Multiple bending corrections can further weaken material.

Thus, it is desirable to have a way to bend rods in the operating room to greatly simplify the surgery and improve mechanical properties (e.g., strength and/or curvature) of the rods and thus outcomes for the patients.

SUMMARY

The disclosed technology relates to a rod bending module for use with a robotic surgical system in an operating room. The system which is capable to bend rods for surgeries directly in the operating room. The rigidity of the rods is such that the robotic arm alone would have to be large and unwieldy in an operating room to provide sufficient forces and torques. This invention introduces a bending module integrated with a robotic system which allows free bending of rods within limits required for surgeries. Additionally other technologies, such as navigation and automatic diagnosis algorithms defining ideal curves (e.g., spinal or other bone curves), can be integrated with the robotic surgical system.

The bending module, rod fixation and robotic system can be put together in different architectures. For example, the bending module may be mounted for example, on the mobile cart. It can be entirely external (e.g., including the actuator) to the cart (e.g., and the robotic surgical system) and sterilizable and/or autoclavable. The rod fixation device can be attached to the end effector of the robot such that the robot can position and rod in the bending module. This allows the robotic arm to move the rod in the bending module so that the rod can be bent at the appropriate locations. The bending module can be partially located inside the robotic surgical system. For example, the actuator for the bending module can be located in the mobile cart such that the motor does not need to be sterile. A sterile component would extend from the cart (or be extendable from the cart when activated) with an appropriate seal to maintain the sterile zone. The bending module can attach to the outside of the mobile cart and the bending die can be activated by the sterile component of the actuator that extends from (or can extend from) the mobile cart. In other embodiments, the bending module is affixed to the end effector and the rod fixation apparatus is attached to, for example, the mobile cart.

In one aspect, the disclosed technology includes a machine for intraoperative bending of rods, the machine including: a bending apparatus for bending a rod, the bending apparatus comprising: a force die; a bend die; and a force transfer device that transfers energy from an actuator to the force die thereby causing a rod positioned between the force die and the bend die to bend around the bend die; and a fixation apparatus for releasably securing the bending apparatus to a robotic surgical system.

In certain embodiments, the fixation apparatus is magnetic, electro-magnetic, and/or mechanical (e.g. using lever device).

In certain embodiments, the fixation apparatus comprises at least one of push clips, push in rivets, screw rivets, clips, and tabs configured to attach to an interface on the robot.

In certain embodiments, the fixation apparatus comprises one or more holes sized for one or more bolts to pass through to secure the bending apparatus to the robotic surgical system via the one or more bolts.

In certain embodiments, the bending device is a ram bending device, three-roll bending device, compression bending device, or rotary draw bending device.

In certain embodiments, the bending device is a ram bending device, the force die comprises a first counter die and a second counter die, and the bend die is a radius block.

In certain embodiments, the bending device is a three-roll bending device, the force die comprises a first counter roller and a second counter roller, and the bend die is a bend roller.

In certain embodiments, the bending device is a compression bending device, the force die comprises a stationary bend die, the bending device comprises a clamp, and the bend die is a compression die.

In certain embodiments, the bending device is a rotary draw bending device, the force die comprises a stationary pressure die, the bending device comprises a clamp, a follower slide, and a wiper die, and the bend die is a rotatable bend die.

In certain embodiments, the bending module is a passive bending module.

In certain embodiments, the bending device comprises an actuator for applying a force to the force die thereby causing a rod positioned between the force die and the bend die to bend around the bend die.

In certain embodiments, the force transfer device is arranged to transfer a force from an actuator to the force die.

In certain embodiments, the bending module is an active bending module.

In certain embodiments, the bending module comprises a cutter for cutting rods.

In certain embodiments, the bending module is at least in part a fixed module.

In certain embodiments, the bending module is arranged to be releasably connected to a mobile cart.

In certain embodiments, the bending module is a floating module.

In certain embodiments, the bending module is arranged to be releasably connected to a robotic arm.

In certain embodiments, the actuator is separate from the bending apparatus.

In certain embodiments, the actuator is internal to a mobile cart.

In certain embodiments, the bending apparatus is autoclavable.

In certain embodiments, the bending apparatus is sterilizable.

In certain embodiments, the bending apparatus has at least one of a length, width, and height from 2 inches to 4 inches, 4 inches to 6 inches, 6 inches to 8 inches, 8 inches to 12 inches, and 1 foot to 2 feet.

In certain embodiments, the actuator is external to the bending module.

In certain embodiments, the fixation apparatus comprises a lever device.

In another aspect, the disclosed technology includes a robotic surgical system for use in a surgical procedure, the system including: a robotic arm comprising an end-effector; an actuator for controlled movement of the robotic arm and positioning of the end effector; and a processor and a non-transitory computer readable medium storing instructions thereon wherein the instructions, when executed, cause the processor to: receive (e.g., determine) a desired curvature of a skeletal structure (e.g., spine, hip, leg, femur, tibia, Tibia, hip, knee, or ankle) of a patient; determine a position of each the two or more screws in the patient during the surgical procedure (e.g., using a pointing device and a navigation system; e.g., wherein the position of each of the two or more screws is different than an ideal position of each screw); and intraoperatively determine the desired curvature of an implantable rod (e.g., for use in joining the heads of two or more screws) based at least in part on the desired curvature of the skeletal structure and the position of the two or more screws placed in the patient during the surgical procedure.

In certain embodiments, the instructions, when executed by the processor, cause the processor to: position the end effector thereby positioning the rod relative to a bending apparatus; and send signals to the bending apparatus that cause the bending apparatus to bend the rod.

In certain embodiments, the instructions, when executed by the processor, cause the processor to: position the end effector and send signals to a bending apparatus thereby causing the bending apparatus to bend the rod, thereby creating a shaped rod.

In certain embodiments, the instructions, when executed by the processor, cause the processor to: receive (e.g., determine) a desired curvature of a skeletal structure of a patient; determine a position of each the two or more screws in the patient during the surgical procedure (e.g., using a pointing device and a navigation system; e.g., wherein the position of each of the two or more screws is different than an ideal position of each screw); and intraoperatively determine the desired curvature of an implantable rod (e.g., for use in joining the heads of two or more screws) based at least in part on the desired curvature of the skeletal structure and the position of the two or more screws placed in the patient during the surgical procedure.

In certain embodiments, the desired curvature of the skeletal structure is determined pre-operatively.

In certain embodiments, the position of each of the two or more screws in the patient is determined intra-operatively.

In certain embodiments, the position of each of the two or more screws in the patient is determined using a navigation system (e.g., separate from or integrated into the robotic surgical system).

In certain embodiments, the position of each of the two or more screws in the patient is determined using a point device with the navigation system to identify the locations of the screws during the surgical procedure.

In certain embodiments, the instructions, when executed by the processor, cause the processor to send one or more signals to the bending apparatus to cause the bending apparatus to bend the rod to produce the shaped rod.

In certain embodiments, the shaped rod is shaped to connect the two or more screws to each other.

In certain embodiments, the system includes a rod fixation apparatus for grasping a rod (e.g., wherein the rod can be placed into the rod fixation "touch-free"—e.g., with a surgeon physically grasping the rod with his/her hand).

In certain embodiments, the rod fixation apparatus is arranged to be held by the end effector.

In certain embodiments, the end effector is a force and/or torque control end-effector.

In certain embodiments, the end effector is configured to hold a first surgical tool.

In certain embodiments, the end-effector comprises a tool holder attached to the robotic arm via a force sensor, wherein the tool holder is sized and shaped to hold a first surgical tool.

In certain embodiments, the system includes a manipulator configured to allow robotically-assisted or unassisted positioning and/or movement of the end-effector by a user with at least four degrees of freedom.

In certain embodiments, the system includes a handle extending from the end effector that may be grasp by a hand of a user—to move and/or position the end effector.

In certain embodiments, the system includes a force sensor located between the robotic arm and the tool holder for measuring forces and/or torques applied by a user to the first surgical tool held by the tool holder.

In certain embodiments, the system includes a sensor that detects the presence of the hand of the user on the handle.

In certain embodiments, the robotic surgical system is configured to permit a surgeon to manually move the end-effector to a position for an operation.

In certain embodiments, the system includes: a bending apparatus for bending a rod, the bending apparatus comprising: a force die; a bend die; and a force transfer device that transfers energy from an actuator (e.g., external to the bending module) to the force die thereby causing a rod positioned between the force die and the bend die to bend around the bend die; and a fixation apparatus for releasably securing the bending apparatus to a robotic surgical system.

In certain embodiments, the fixation apparatus is magnetic, electro-magnetic, and/or mechanical (e.g. using lever device).

In certain embodiments, the fixation apparatus comprises at least one of push clips, push in rivets, screw rivets, clips, and tabs configured to attach to an interface on the robot.

In certain embodiments, the fixation apparatus comprises one or more holes sized for one or more bolts to pass through to secure the bending apparatus to the robotic surgical system via the one or more bolts.

In certain embodiments, the bending device is a ram bending device, three-roll bending device, compression bending device, or rotary draw bending device.

In certain embodiments, the bending device is a ram bending device, the force die comprises a first counter die and a second counter die, and the bend die is a radius block.

In certain embodiments, the bending device is a three-roll bending device, the force die comprises a first counter roller and a second counter roller, and the bend die is a bend roller.

In certain embodiments, the bending device is a compression bending device, the force die comprises a stationary bend die, the bending device comprises a clamp, and the bend die is a compression die.

In certain embodiments, the bending device is a rotary draw bending device, the force die comprises a stationary pressure die, the bending device comprises a clamp, a follower slide, and a wiper die, and the bend die is a rotatable bend die.

In certain embodiments, the bending module is a passive bending module.

In certain embodiments, the bending device comprises an actuator for applying a force to the force die thereby causing a rod positioned between the force die and the bend die to bend around the bend die.

In certain embodiments, the force transfer device is arranged to transfer a force from an actuator to the force die.

In certain embodiments, the bending module is an active bending module.

In certain embodiments, the bending module comprises a cutter for cutting rods.

In certain embodiments, the bending module is at least in part a fixed module.

In certain embodiments, the bending module is arranged to be releasably connected to a mobile cart.

In certain embodiments, the bending module is a floating module.

In certain embodiments, the bending module is arranged to be releasably connected to a robotic arm.

In certain embodiments, the actuator is separate from the bending apparatus.

In certain embodiments, the actuator is internal to a mobile cart.

In certain embodiments, the bending apparatus is autoclavable.

In certain embodiments, the bending apparatus is sterilizable.

In certain embodiments, the bending apparatus has at least one of a length, width, and height from 2 inches to 4 inches, 4 inches to 6 inches, 6 inches to 8 inches, 8 inches to 12 inches, and 1 foot to 2 feet.

In certain embodiments, the surgery is orthopedic surgery or spinal surgery.

In certain embodiments, the end-effector is configured to releasably hold the first surgical tool, allowing the first surgical tool to be removed and replaced with a second surgical tool.

In certain embodiments, the manipulator is configured to allow robotically assisted or unassisted positioning and/or movement of the end-effector by a user with at least six degrees of freedom, wherein the six degrees of freedom are three degrees of translations and three degrees of rotations.

In certain embodiments, the patient position is a position of one or more markers placed in spatial relation to one or more vertebrae.

In certain embodiments, controlling the actuator to move the end-effector comprises controlling the actuator to move the end-effector in a direction corresponding to a direction of application of the force and/or torque.

In certain embodiments, the end-effector is configured to move at a predetermined measured pace upon application and detection of user force and/or torque applied to the end-effector in excess of the predetermined minimum force and/or torque and the predetermined measured pace is a steady, slow velocity.

In another aspect, the disclosed technology includes a robotic surgical system for performing surgery, the system including: a robotic arm comprising an end-effector; an actuator for controlled movement of the robotic arm and positioning of the end effector; and a processor and a non-transitory computer readable medium storing instructions thereon wherein the instructions, when executed, cause the processor to: intraoperatively coordinate the bending of an implantable rod to produce a shaped rod based at least in part on a desired curvature of a skeletal structure and the position of each of two or more screws in the patient during the surgical procedure.

In certain embodiments, the instructions, when executed by the processor, cause the processor to: position the end effector thereby positioning the rod relative to a bending apparatus; and send signals to the bending apparatus that cause the bending apparatus to bend the rod.

In certain embodiments, the instructions, when executed by the processor, cause the processor to: position the end effector and send signals to a bending apparatus thereby causing the bending apparatus to bend the rod, thereby creating a shaped rod.

In certain embodiments, the instructions, when executed by the processor, cause the processor to: receive (e.g., determine) a desired curvature of a skeletal structure of a patient; determine a position of each the two or more screws in the patient during the surgical procedure (e.g., using a pointing device and a navigation system; e.g., wherein the position of each of the two or more screws is different than an ideal position of each screw); and intraoperatively determine the desired curvature of an implantable rod (e.g., for use in joining the heads of two or more screws) based at least in part on the desired curvature of the skeletal structure and the position of the two or more screws placed in the patient during the surgical procedure.

In certain embodiments, the desired curvature of the skeletal structure is determined pre-operatively.

In certain embodiments, the position of each of the two or more screws in the patient is determined intra-operatively.

In certain embodiments, the position of each of the two or more screws in the patient is determined using a navigation system (e.g., separate from or integrated into the robotic surgical system).

In certain embodiments, the position of each of the two or more screws in the patient is determined using a point device with the navigation system to identify the locations of the screws during the surgical procedure.

In certain embodiments, the instructions, when executed by the processor, cause the processor to send one or more signals to the bending apparatus to cause the bending apparatus to bend the rod to produce the shaped rod.

In certain embodiments, the shaped rod is shaped to connect the two or more screws to each other.

In certain embodiments, the system includes a rod fixation apparatus for grasping a rod (e.g., wherein the rod can be placed into the rod fixation "touch-free"—e.g., with a surgeon physically grasping the rod with his/her hand).

In certain embodiments, the rod fixation apparatus is arranged to be held by the end effector.

In certain embodiments, the end effector is a force and/or torque control end-effector.

In certain embodiments, the end effector is configured to hold a first surgical tool.

In certain embodiments, the end-effector comprises a tool holder attached to the robotic arm via a force sensor, wherein the tool holder is sized and shaped to hold a first surgical tool.

In certain embodiments, the system includes a manipulator configured to allow robotically-assisted or unassisted positioning and/or movement of the end-effector by a user with at least four degrees of freedom.

In certain embodiments, the system includes a handle extending from the end effector that may be grasp by a hand of a user—to move and/or position the end effector.

In certain embodiments, the system includes a force sensor located between the robotic arm and the tool holder for measuring forces and/or torques applied by a user to the first surgical tool held by the tool holder.

In certain embodiments, the system includes a sensor that detects the presence of the hand of the user on the handle.

In certain embodiments, the robotic surgical system is configured to permit a surgeon to manually move the end-effector to a position for an operation.

In certain embodiments, the system includes: a bending apparatus for bending a rod, the bending apparatus comprising: a force die; a bend die; and a force transfer device that transfers energy from an actuator (e.g., external to the bending module) to the force die thereby causing a rod positioned between the force die and the bend die to bend around the bend die; and a fixation apparatus for releasably securing the bending apparatus to a robotic surgical system.

In certain embodiments, the fixation apparatus is magnetic, electro-magnetic, and/or mechanical (e.g. using lever device).

In certain embodiments, the fixation apparatus comprises at least one of push clips, push in rivets, screw rivets, clips, and tabs configured to attach to an interface on the robot.

In certain embodiments, the fixation apparatus comprises one or more holes sized for one or more bolts to pass through to secure the bending apparatus to the robotic surgical system via the one or more bolts.

In certain embodiments, the bending device is a ram bending device, three-roll bending device, compression bending device, or rotary draw bending device.

In certain embodiments, the bending device is a ram bending device, the force die comprises a first counter die and a second counter die, and the bend die is a radius block.

In certain embodiments, the bending device is a three-roll bending device, the force die comprises a first counter roller and a second counter roller, and the bend die is a bend roller.

In certain embodiments, the bending device is a compression bending device, the force die comprises a stationary bend die, the bending device comprises a clamp, and the bend die is a compression die.

In certain embodiments, the bending device is a rotary draw bending device, the force die comprises a stationary pressure die, the bending device comprises a clamp, a follower slide, and a wiper die, and the bend die is a rotatable bend die.

In certain embodiments, the bending module is a passive bending module.

In certain embodiments, the bending device comprises an actuator for applying a force to the force die thereby causing a rod positioned between the force die and the bend die to bend around the bend die.

In certain embodiments, the force transfer device is arranged to transfer a force from an actuator to the force die.

In certain embodiments, the bending module is an active bending module.

In certain embodiments, the bending module comprises a cutter for cutting rods.

In certain embodiments, the bending module is at least in part a fixed module.

In certain embodiments, the bending module is arranged to be releasably connected to a mobile cart.

In certain embodiments, the bending module is a floating module.

In certain embodiments, the bending module is arranged to be releasably connected to a robotic arm.

In certain embodiments, the actuator is separate from the bending apparatus.

In certain embodiments, the actuator is internal to a mobile cart.

In certain embodiments, the bending apparatus is autoclavable.

In certain embodiments, the bending apparatus is sterilizable.

In certain embodiments, the bending apparatus has at least one of a length, width, and height from 2 inches to 4 inches, 4 inches to 6 inches, 6 inches to 8 inches, 8 inches to 12 inches, and 1 foot to 2 feet.

In certain embodiments, the surgery is orthopedic surgery or spinal surgery.

In certain embodiments, the end-effector is configured to releasably hold the first surgical tool, allowing the first surgical tool to be removed and replaced with a second surgical tool.

In certain embodiments, the manipulator is configured to allow robotically assisted or unassisted positioning and/or movement of the end-effector by a user with at least six degrees of freedom, wherein the six degrees of freedom are three degrees of translations and three degrees of rotations.

In certain embodiments, the patient position is a position of one or more markers placed in spatial relation to one or more vertebrae.

In certain embodiments, controlling the actuator to move the end-effector comprises controlling the actuator to move the end-effector in a direction corresponding to a direction of application of the force and/or torque.

In certain embodiments, the end-effector is configured to move at a predetermined measured pace upon application and detection of user force and/or torque applied to the end-effector in excess of the predetermined minimum force and/or torque and the predetermined measured pace is a steady, slow velocity.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
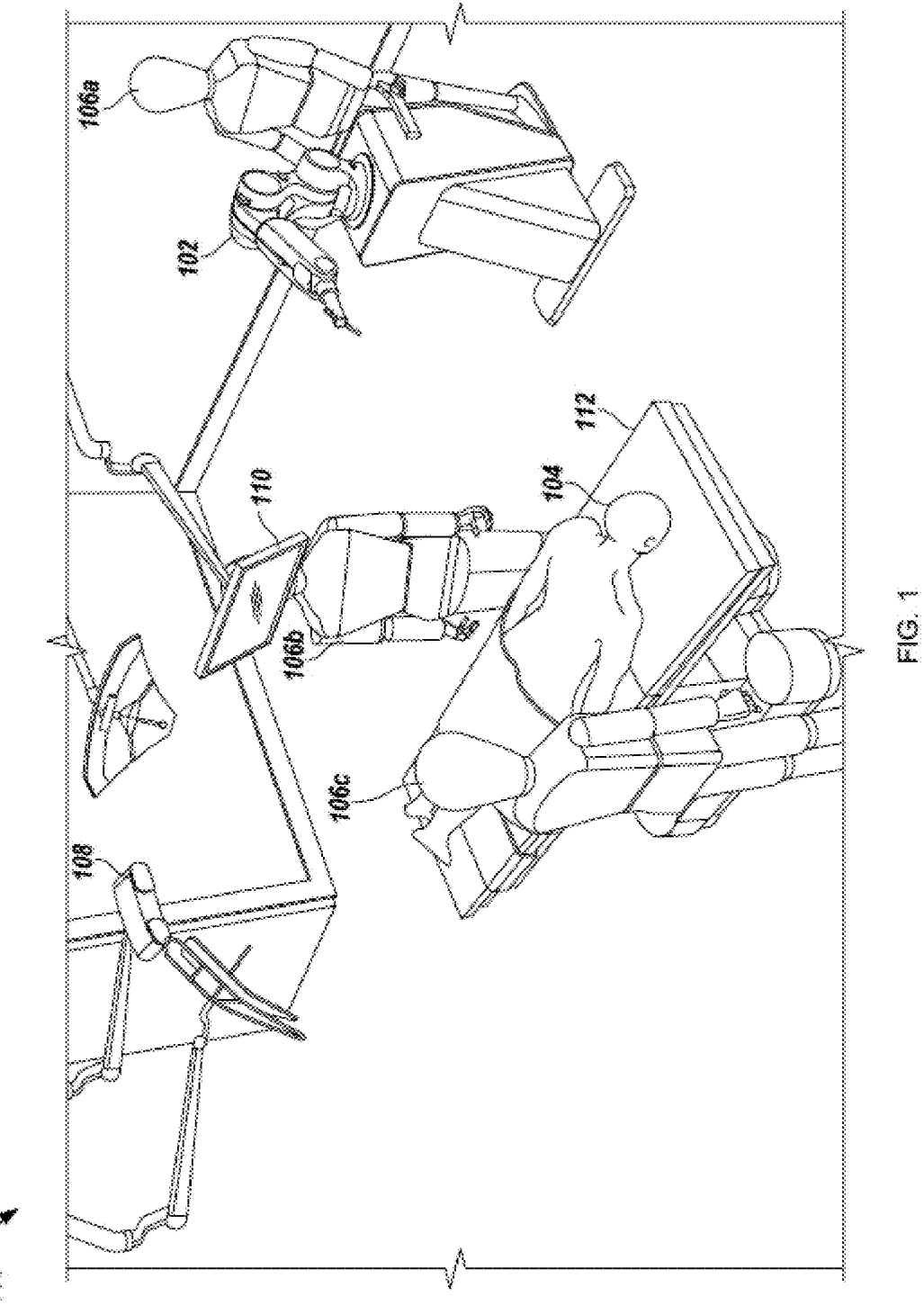
FIG. 1 is an illustration of an example robotic surgical system in an operating room.
Figure 2:
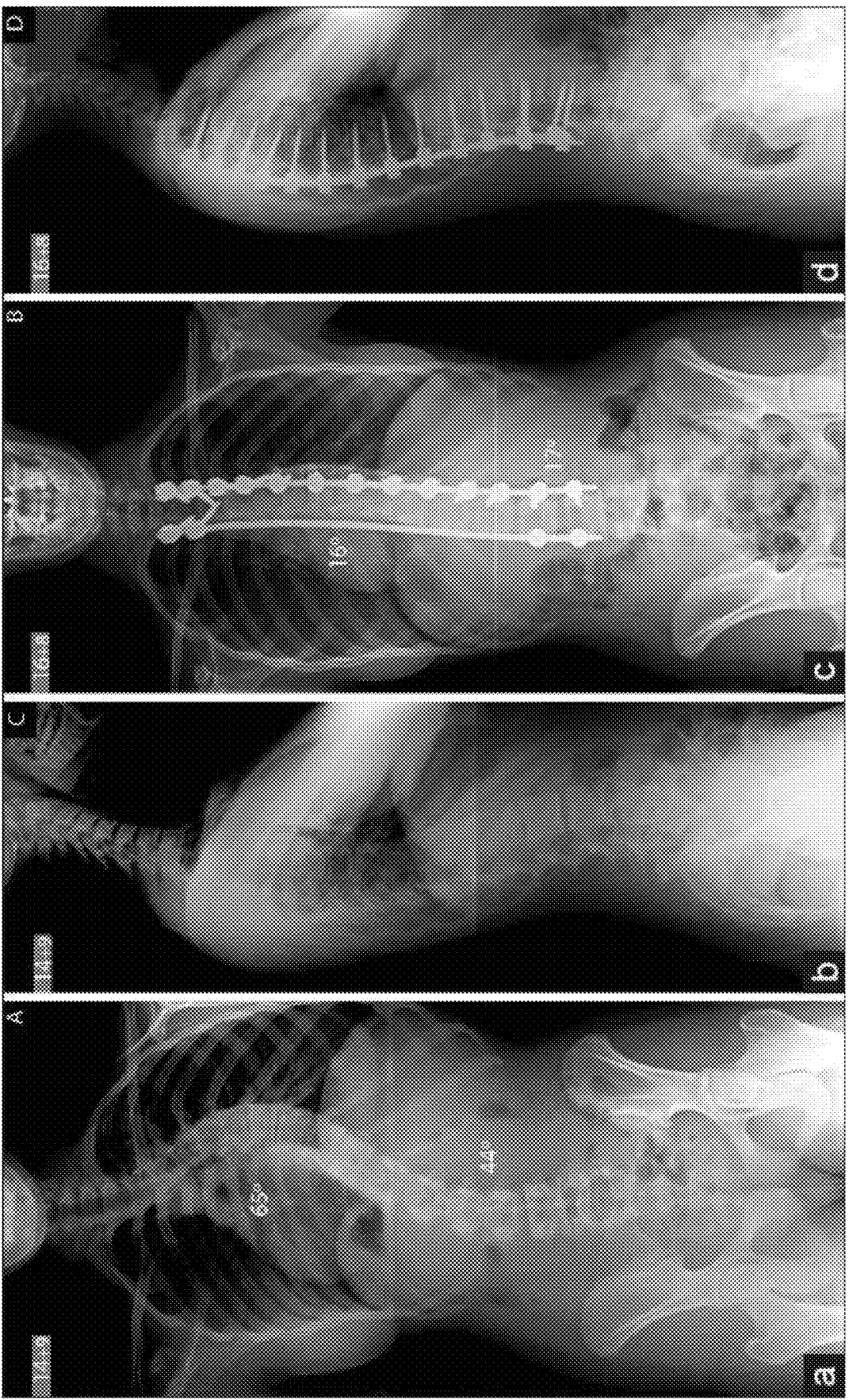
FIG. 2 is an illustration of how rods can be bent and implemented to correct the shape of a spine.
Figure 3:
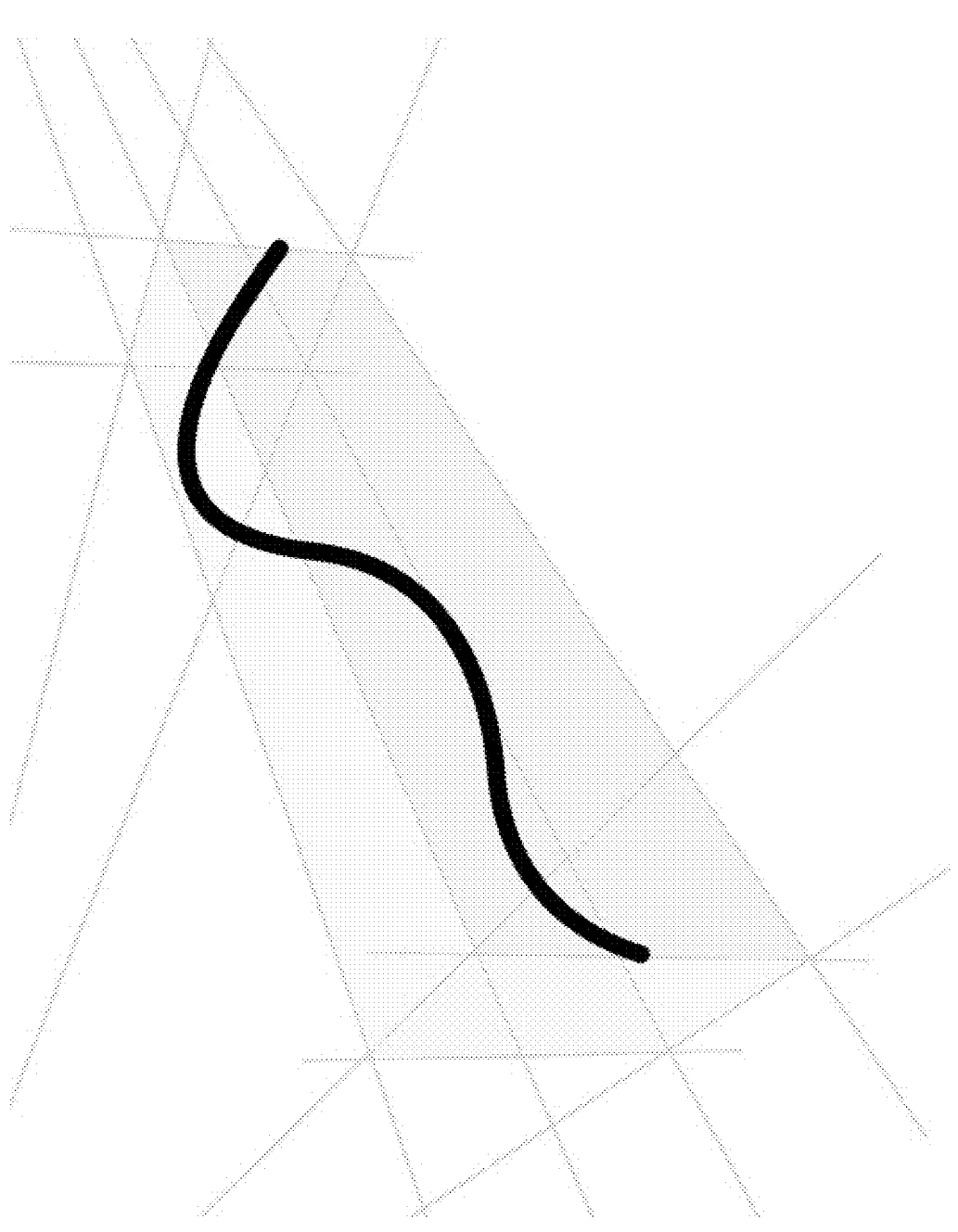
FIG. 3 is an illustration of a curvature that may be applied to a rod for use in correcting the shape of a spine.
Figure 4:
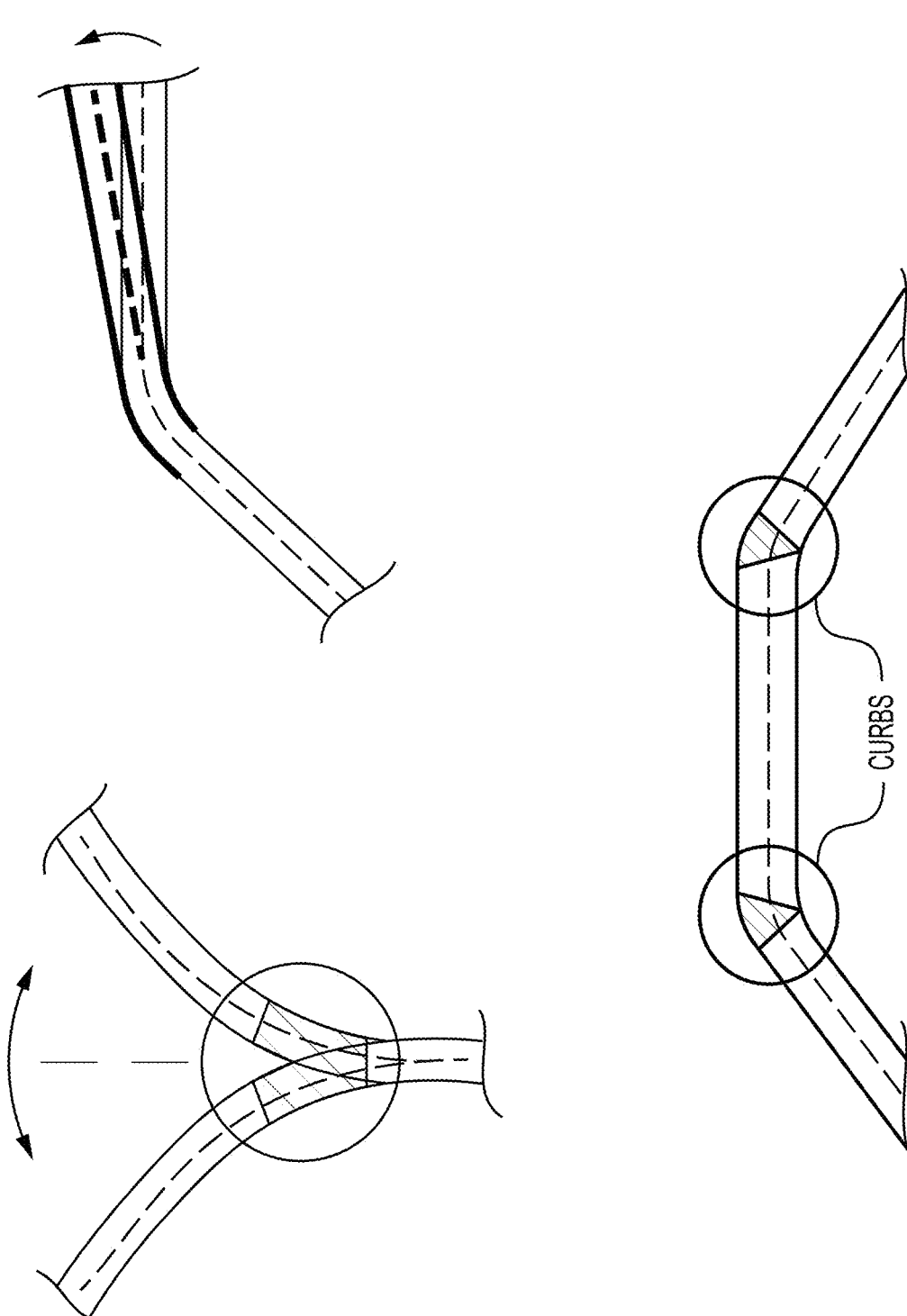
FIG. 4 is an illustration of the undesirable features that may occur when manually bending rods.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

FIG. 1 illustrates an example robotic surgical system in an operating room 100. In some implementations, one or more surgeons, surgical assistants, surgical technologists and/or other technicians (e.g., 106a-c) perform an operation on a patient 104 using a robotic-assisted surgical system. In the operating room 100 the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no preoperative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient 104. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion, or orthopedic surgery, such as knee, shoulder, hip, leg, or ankle surgery. In some implementations, the surgical robotic system includes a surgical robot 102 on a mobile cart 114. The surgical robot 102 in the example shown in FIG. 1 is positioned in proximity to an operating table 112 without being attached to the operating table 112, thereby providing maximum operating area and mobility to surgeons around the operating table 112 and reducing clutter on the operating table 112. In alternative embodiments, the surgical robot 102 (or cart) is securable to the operating table 112. In certain embodiments, both the operating table 112 and the cart 114 are secured to a common base to prevent any movement of the cart or table 112 in relation to each other, even in the event of an earth tremor.

The mobile cart 114 may permit a user (operator) 106a, such as a technician, nurse, surgeon, or any other medical personnel in the operating room 100, to move the surgical robot 102 to different locations before, during, and/or after a surgical procedure. The mobile cart 104 enables the surgical robot 102 to be easily transported into and out of the operating room 100. For example, a user 106a may move the surgical robot 102 into the operating room 100 from a storage location. In some implementations, the mobile cart 114 may include wheels, a track system, such as a continuous track propulsion system, or other similar mobility systems for translocation of the cart. The mobile cart 114 may include an attached or embedded handle for locomotion of the mobile cart 114 by an operator (e.g., user 106a).

For safety reasons, the mobile cart 114 may be provided with a stabilization system that may be used during a surgical procedure performed with a surgical robot 102. The stabilization device increases the global stiffness of the mobile cart 114 relative to the floor in order to ensure the accuracy of the surgical procedure. In some implementations, the wheels include a locking device that prevents the cart 114 from moving. The stabilizing, braking, and/or locking device may be activated when the machine is turned on. In some implementations, the mobile cart 114 includes multiple stabilizing, braking, and/or locking devices. In some implementations, the stabilizing device is electro-mechanical with electronic activation. The stabilizing, braking, and/or locking device(s) may be entirely mechanical. The stabilizing, braking, and/or locking device(s) may be electronically activated and deactivated.

In some implementations, the surgical robot 102 includes a robotic arm mounted on a mobile cart 114. An actuator may move the robotic arm. The robotic arm may include a force control end-effector configured to hold a surgical tool. The robot 102 may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 (e.g., navigation system) that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector 108 may be a camera, a video camera, an infrared detector, field generator and sensors for electromagnetic tracking or any other motion detecting apparatus. In some implementation, based on the patient and robot position, the display screen 110 displays a projected trajectory and/or a proposed trajectory for the robotic arm of robot 102 from its current location to a patient operation site. By continuously monitoring the patient 104 and robotic arm positions, using tracking detector 108, the surgical system can calculate updated trajectories and visually display these trajectories on display screen 110 to inform and guide surgeons and/or technicians in the operating room 100 using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae and/or other part of the patient 104 during the surgical procedure. An example robotic surgical system that may be used with the disclosed technology or modified for use with the disclosed technology is described in U.S. patent application Ser. No. 14/266,769, filed Apr. 30, 2014 and entitled Apparatus, Systems, and Methods for Precise Guidance of Surgical Tools, the contents of which are hereby incorporated by reference in their entirety.

Figure 5:
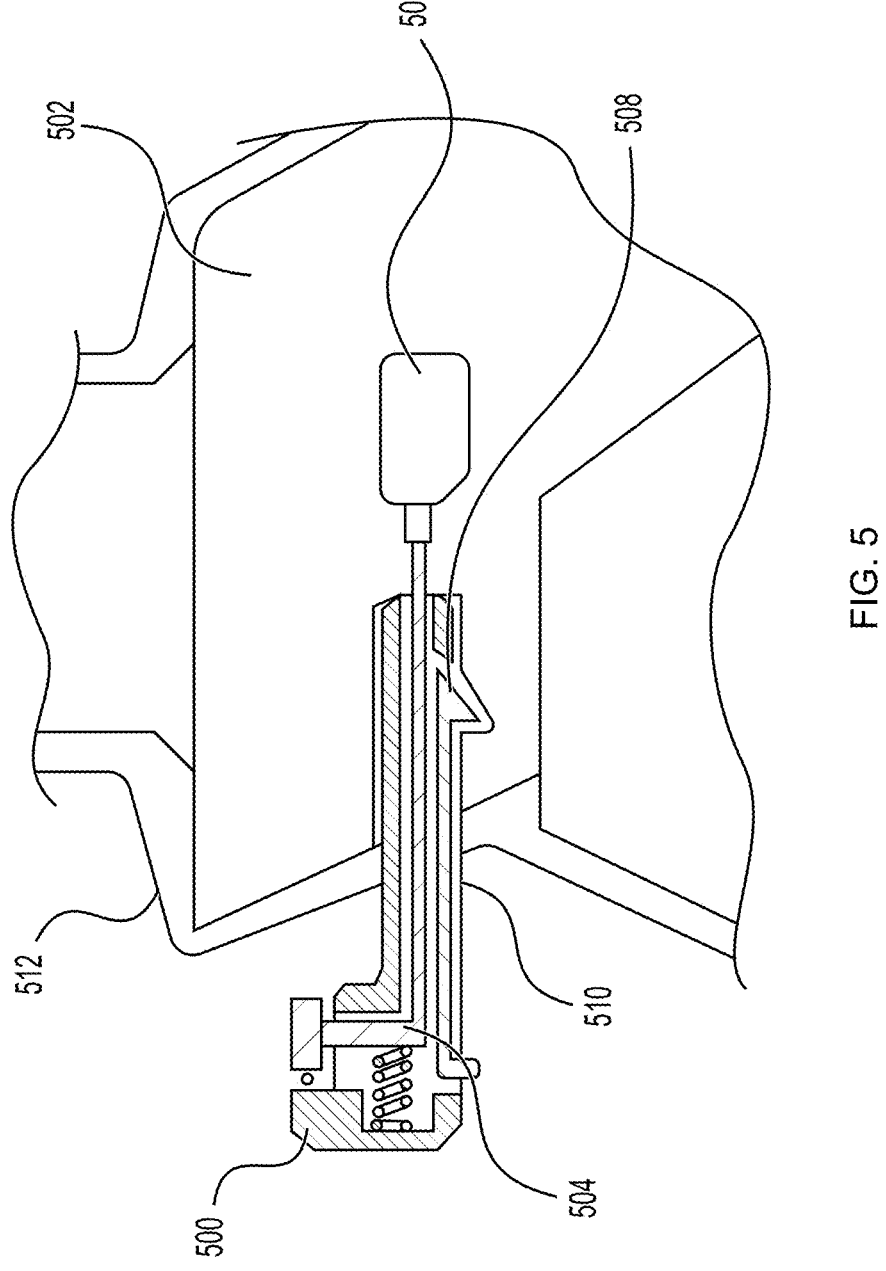
FIG. 5 is an illustration of a passive bending module.

FIG. 5 is an illustration of a passive bending module 500, for example, without actuators therein (e.g., no active parts). Specifically, FIG. 5 illustrates a cross-cut of a portion of a robotic surgical system 502 and a bending module 500. The bending module 500 is a passive device having no active parts (e.g. actuators). This allows the device to be easily sterilized in an autoclave. The module contains a bending element 504 (i.e., force transfer device) which is moved by a linear actuator 506. The module is fixed partially inside robot (e.g., inside a mobile cart of the robotic surgical system). A quick fixation apparatus automatically fixes itself in the desired position after insertion and requires a deliberate action to be removed. In this example, the linear actuator is inside the mobile cart of the robot 502. Thus, in certain embodiments, the linear actuator 506 does not need to be sterile. A sterile drape 512 can include a passageway 510 to allow the bending module 500 to extend therethrough to separate the sterile environment from the non-sterile environment. An example of a sterile drape 512 and the types of drape passages 510 that can be used herein to allow portions of the bending module 500 to be inside the sterile environment and outside the sterile environment are described in described in U.S. patent application Ser. No. 14/602,627, filed Jul. 27, 2015 and entitled "Sterile Drape and Adapter for Covering a Robotic Surgical Arm and Preventing Contamination of a Sterile Field," the contents of which are hereby incorporated by reference in their entirety.

Figure 6:
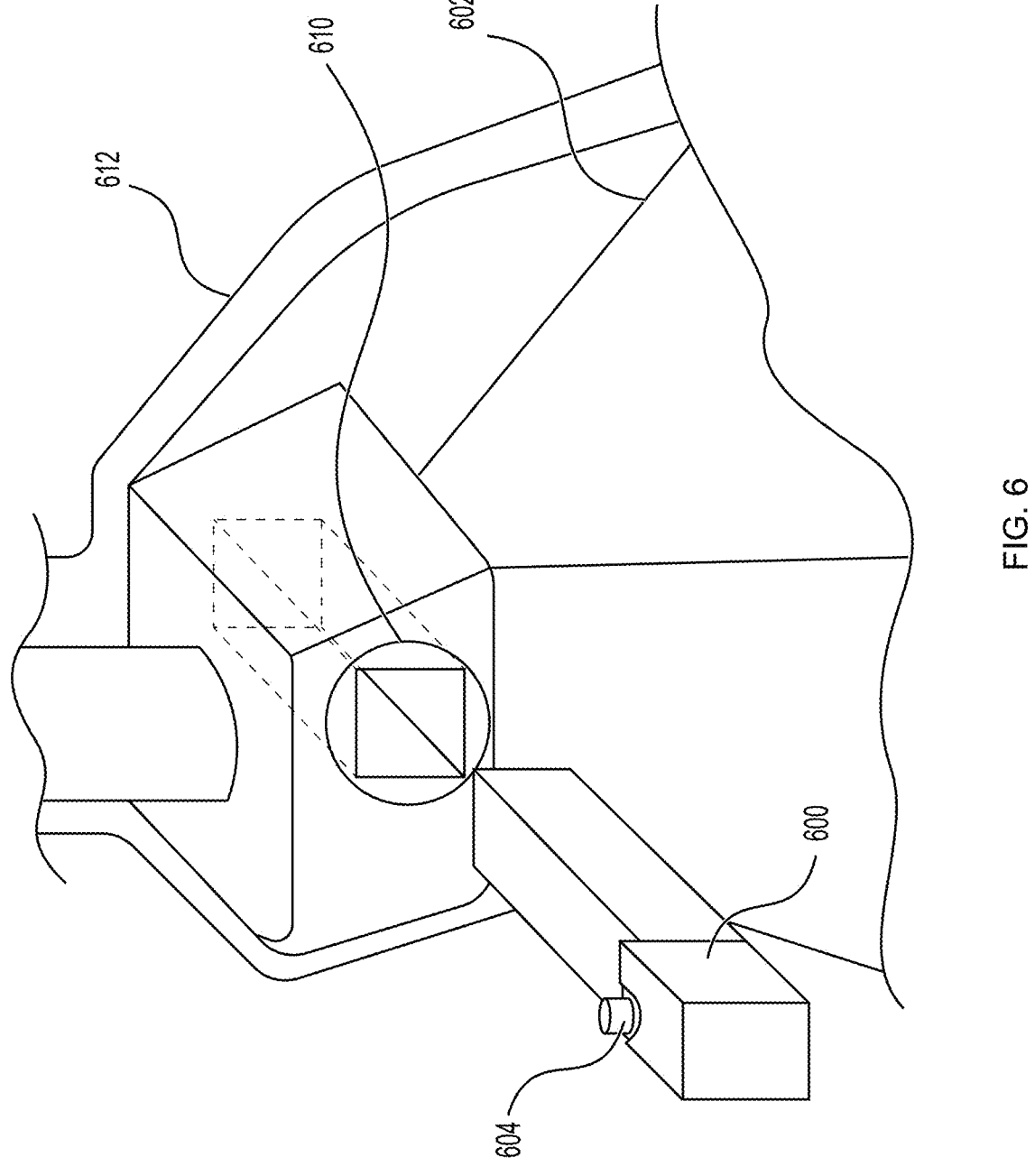
FIG. 6 is an illustration of a bending module before being inserted into a slot in the robotic system.

FIG. 6 illustrates the bending module 600 right before being inserted into slot in the robotic system 602. In certain embodiments, the disclosed technology includes a sterile drape 612 with a sleeve or hole 610 which allows for passing the bending module 600 through the drape 612 so that it can securely couple to the robot 602. In certain embodiments, the sleeve 610 of the drape 612 is sealed using sterile tape (e.g., such that the sleeve is secured tightly around a portion of the bending module). The tape may be wrapped around the sleeve 610 to seal the sleeve 610. In some implementations, the sleeve 610 is part of the sterile drape 612. In some implementations, the sleeve 610 is separate from the drape 612 and the interface between the sleeve 610 and the sterile drape 612 is sealed using sterile adhesive tape or another sterile adhesive material.

In certain embodiments, a sterile adapter is used to secure the drape to the robot around the opening in the drape that allows the bending module to be connected to the robot.

The sterile adapter may be a disposable (e.g. a single-use product). For example, a new sterile adapter may be used for every surgical procedure. In some implementations, the sterile adapter is a rigid or semi-rigid device. It may be made from a hard plastic, polymer, or a composite material. In some implementations, the sterile adapter secures a drape over a surgical robot to prevent contamination of a sterile field.

The sterile adapter may include a rigid or semi-rigid collar (e.g., ring or a hollow cylindrical structure) configured to mount (e.g., snap-mount) onto an interface of the surgical robotic arm. The sterile adapter may include a rigid or semi-rigid body extending from the collar and shaped to conform to a portion of the surgical robotic arm to tightly secure a flexible drape in place (e.g., with no folds) over the portion of the surgical robotic arm when the drape is attached to the adapter.

In some implementations, the body is one or more tabs (e.g., 3, 4, 5, 6, 7, or 8 tabs) that engage an interface on the robot. The tabs may "click" into the interface to provide easy and secure mounting of the sterile adapter, and hence sterile drape, on the robot. The sterile drape may be glued or welded to the sterile adapter (e.g., during manufacturing). The adapter 200 ensures that the drape is tightly stretched over the tool holder and robot interface to provide repeatable and rigid positioning of the tool holder relative to the robotic arm. The sterile drape can be coupled, via glue or welding, to a sterile adapter. In some implementations, the sterile drape is glued or welded to the sterile adapter. After the welding/gluing dries the part of the drape inside the sterile adapter is stretched. The sterile drape can be tightly stretched over the opening of the sterile adapter (e.g., the opening through which the bending module passes to connected to the robot). When the sterile adapter is attached to the robot (e.g., clicked into the interface on the robot), the robot will be covered by the sterile drape that is stretched over the opening of the sterile adapter. As described below, in some implementations, positioning elements and a tightening screw will protrude through the opening of the sterile adapter and piece the sterile drape when the tool support is applied to the robotic arm.

Figure 7:
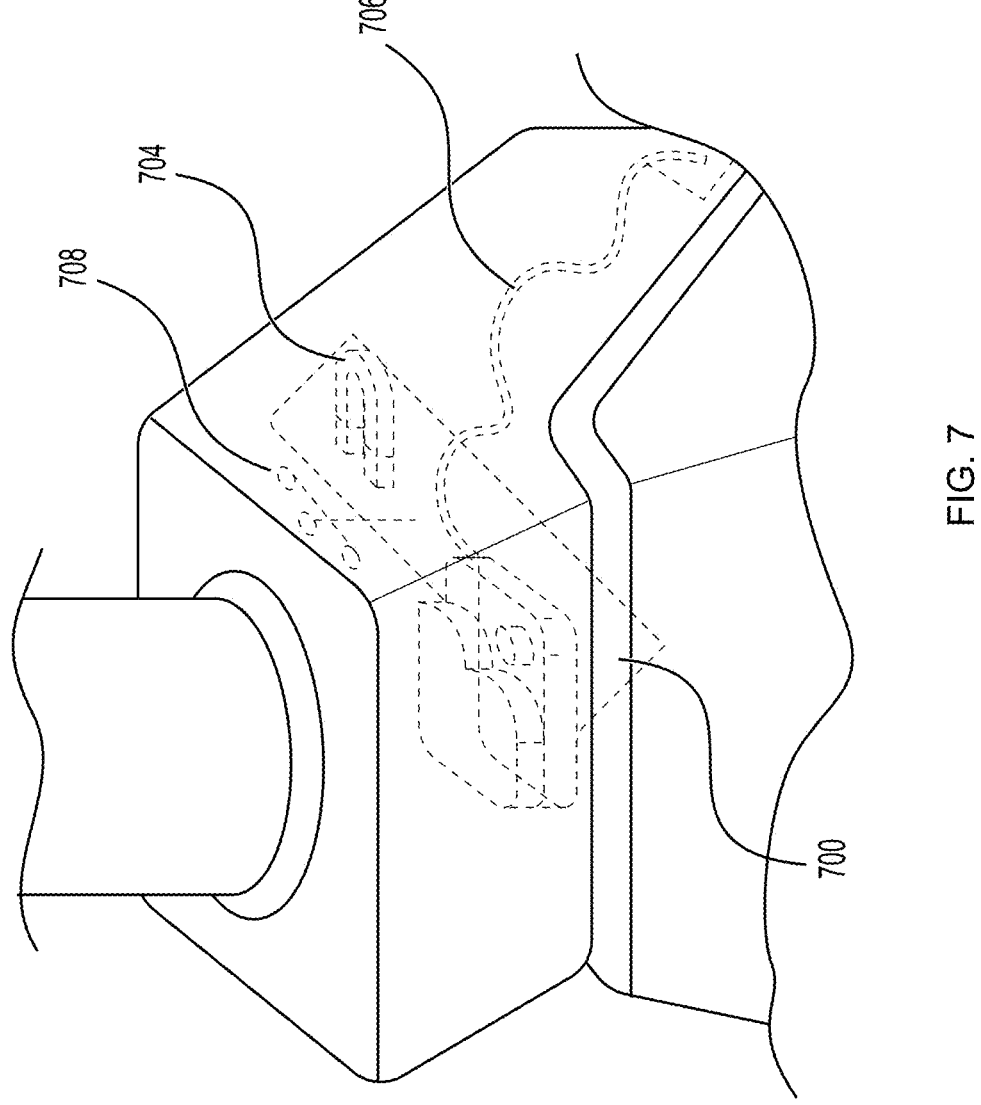
FIG. 7 is an illustration of an active bending module.

FIG. 7 is an illustration of an active bending module 700. Sterility of the active bending module 700 can be achieved by using drapes and sterilizable elements. Additionally, a sterilizable electric motor can be used, such as the EC 19 Brushless DC Motor from Maxon Motor AG of Sachseln, Switzerland.

An active bending module 700 has actuators built in. It is fixed to the robot 702 using a fixation apparatus 704. The fixation apparatus 704 can be magnetic, electro-magnetic, mechanical (e.g. using lever device). In certain embodiments, there is no need for a strong fixation between the robot 702 (e.g., mobile cart) and the bending module 700. During bending most of the large forces and reactions happen within the bending module and do not transmit to the fixation. The positioning of the bending module in reference to the robotic system shall be known by the surgical system (e.g., the robotic surgical system's computer and/or navigation system). This can be achieved by placing the module 700 in a known, pre-determined position, relative to the cart (e.g. using positioning pins, rails, etc.) and/or identifying the position of the module 700 using a navigation marker 708 or by driving robotic arm manually to one or more known points on the bending module 700 to register the position of the bending module 700.

The bending module 700 can be connected to the cart of the robot 702 using, in certain embodiments, a connection cable. In certain embodiments, a mechanical connection is used to actuate the bending module 700. The connection cable 706 can provide power to bending module actuators, actuate them directly, or just send relevant data to bending module internal electronics/logic. In certain embodiments, the movement of the bending element inside bending module 700 is synchronized with movement of the robotic arm.

Figure 8:
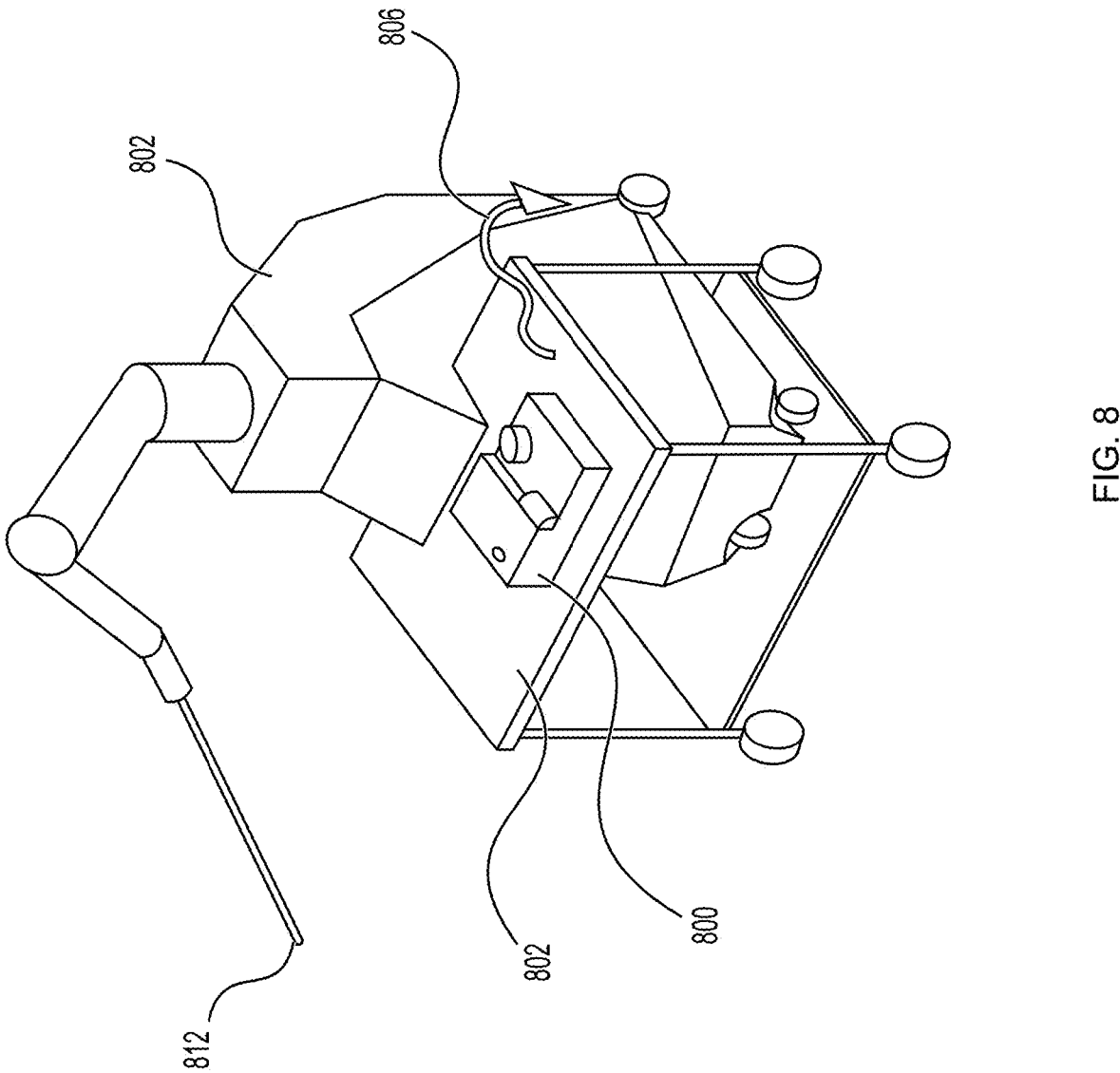
FIG. 8 is an illustration of a bending module on a cart.

Alternatively, as shown in FIG. 8, the bending module 800 can be placed on the separate cart 802 as shown in the Figure above. The cart can be fixed to the robot 802 (e.g., mobile cart of the robot 802) using a fixation apparatus as described above. The precise position of the bending module 800 (navigation, robot registration) can be determine similar manners as described above regardless of the location of the bending module 800. Bending module 800 on the cart uses connection cable 806 for the similar purpose. As shown in FIG. 8, a rod 812 can be held by the robot 802 and inserted in the bending module 800 by the robot 802 so the rod 812 can be bent.

Figure 9:
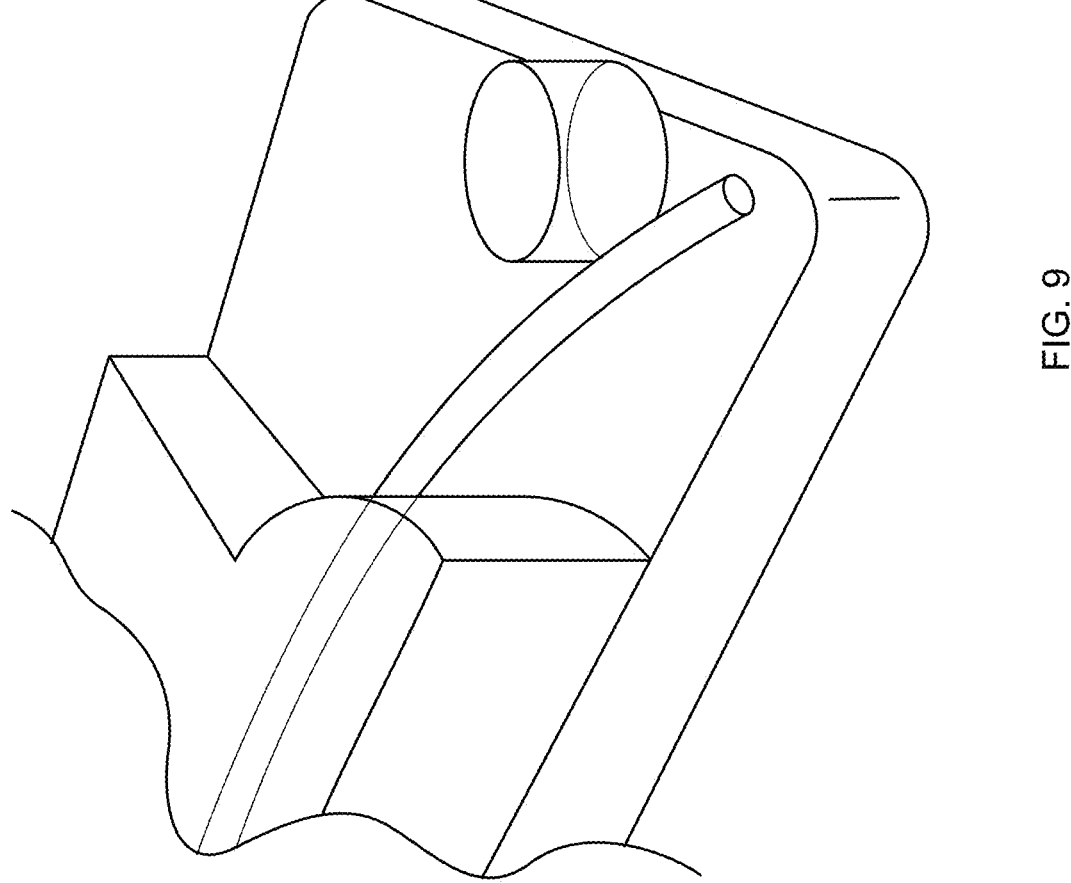
FIG. 9 is an illustration of an example analysis of the forces required to move a bending die of a bending module.

FIG. 9 is an illustration of an example analysis of the forces required to move a bending die of a bending module a particular length depending on the material of the rod.

Figure 10:
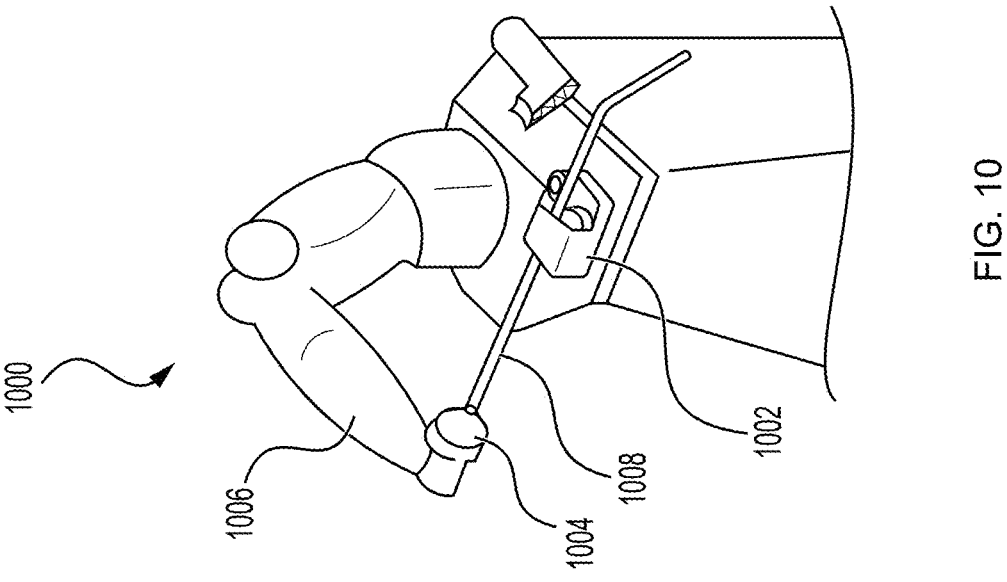
FIG. 10 is an illustrations of a fixed bending module.

FIG. 10 is an illustration of a fixed bending module 1002. In this example the bending module 1002 is fixed and/or at least partially integrated directly into the robot 1000 (e.g., mobile cart). A rod fixation 1004 is attached to the robotic arm 1006 to grasp the rod 1008 such that the robotic arm 1006 can move the rod 1008 and precisely control the positioning of the rod 1008 within the bending module 1002.

Figure 11:
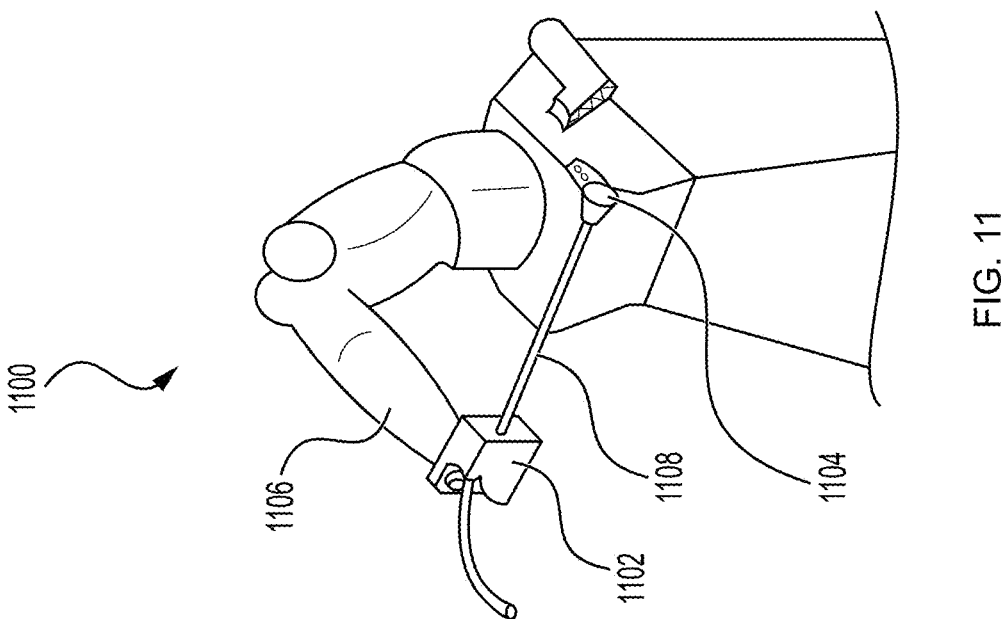
FIG. 11 is an illustration of a floating module.

FIG. 11 is an illustration of a floating bending module 1102. The bending module 1102 is coupled to the robotic arm 1106 and the rod fixation 1104 is connected or integral to the robot 1100 (e.g., mobile cart). The robotic arm 1106 positions the bending module 1102 along the rod 1108 in the appropriate places and the bending module 1102 is activated in these locations to bend the rod 1108 to the appropriate shape.

FIGS. 12A through 12H illustrate various types of bending devices. For example, the bending device used in the bending module may be a compression bending device, a rotary draw bending device, a ram bending device, or a three-roll bending device as shown in FIGS. 12A through 12D respectively.

Figures 12A, 12B, 12C, 12D:
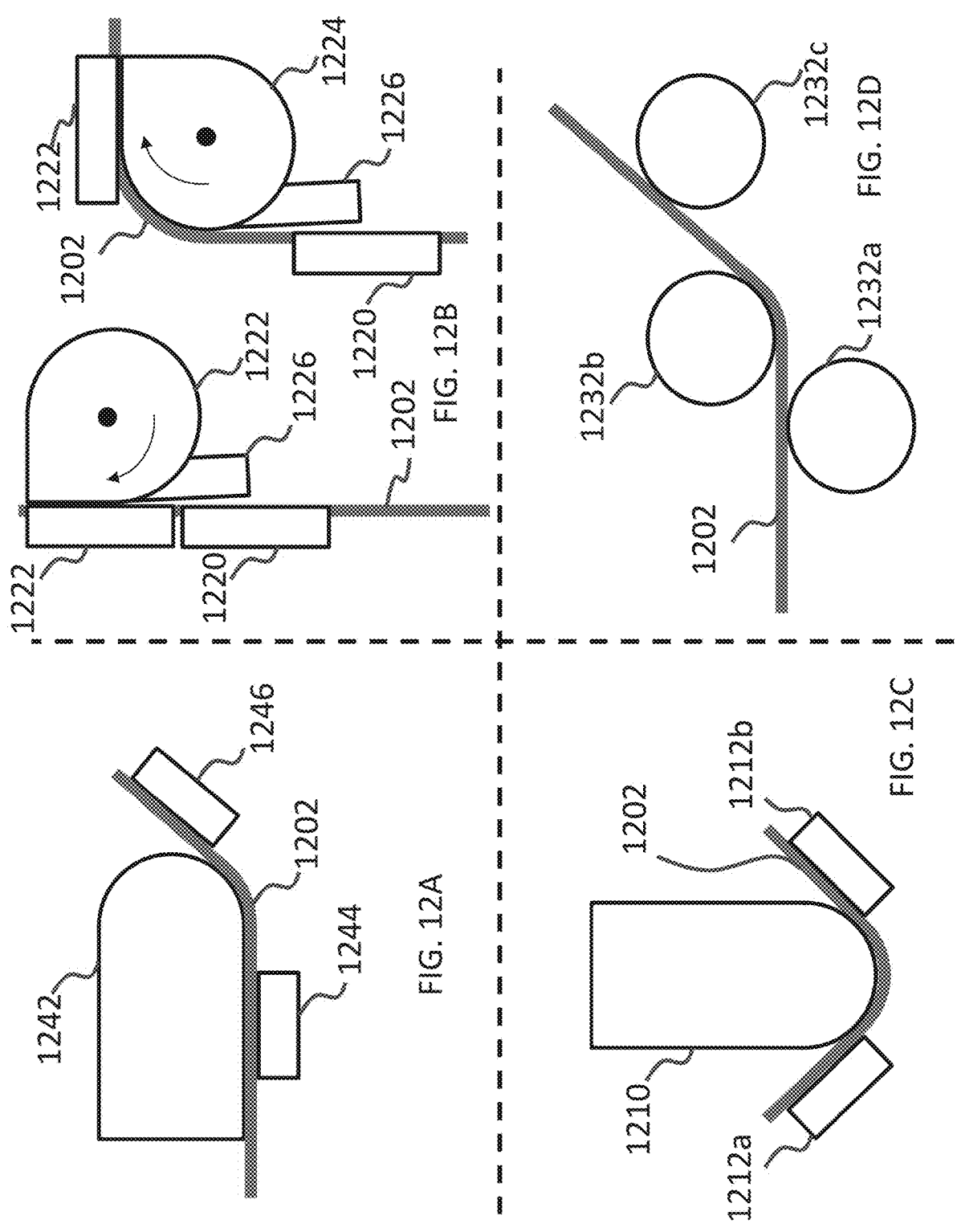
FIGS. 12A through 12H are illustrations of types of bending devices.
Figures 12E, 12F:
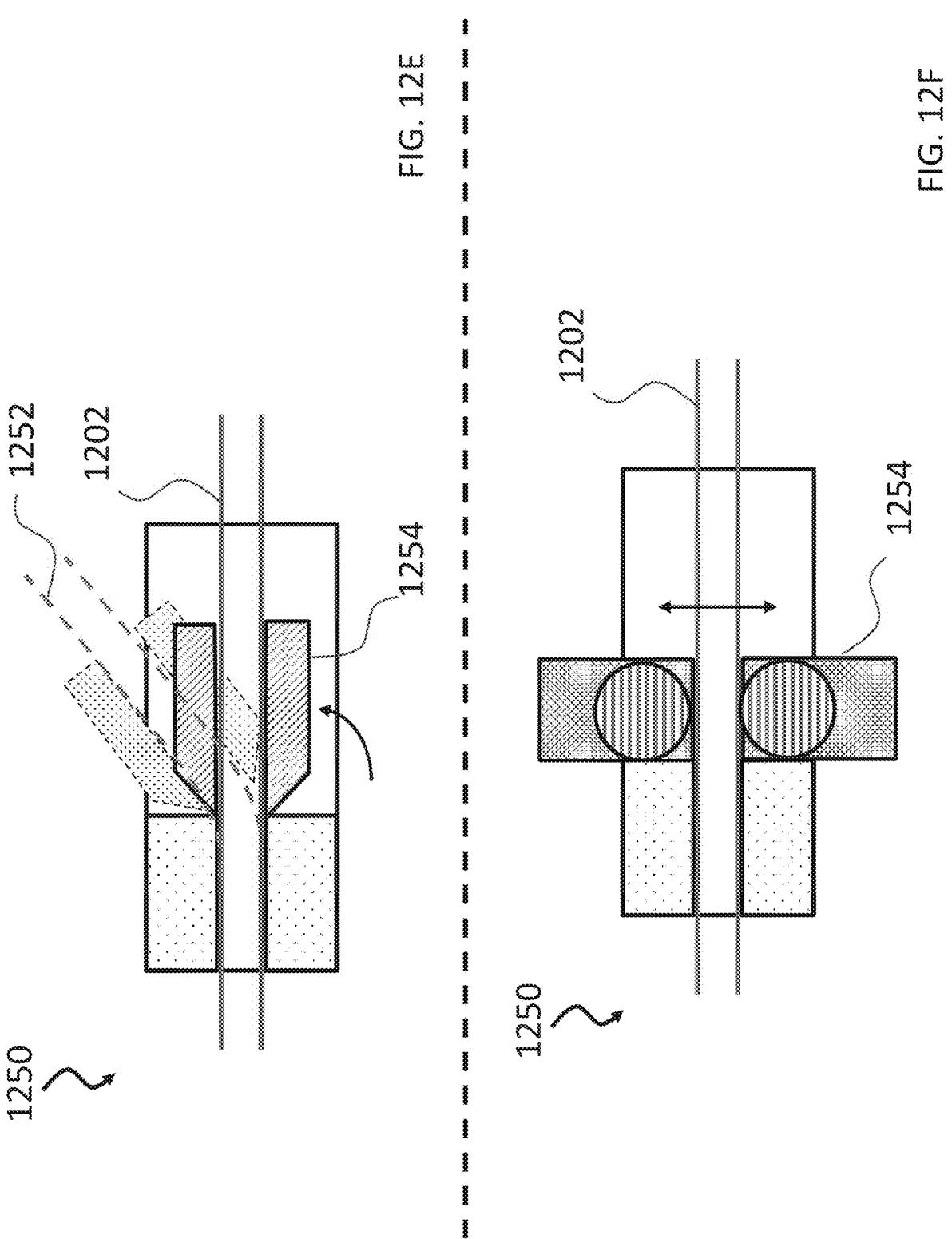
Figures 12G, 12H:
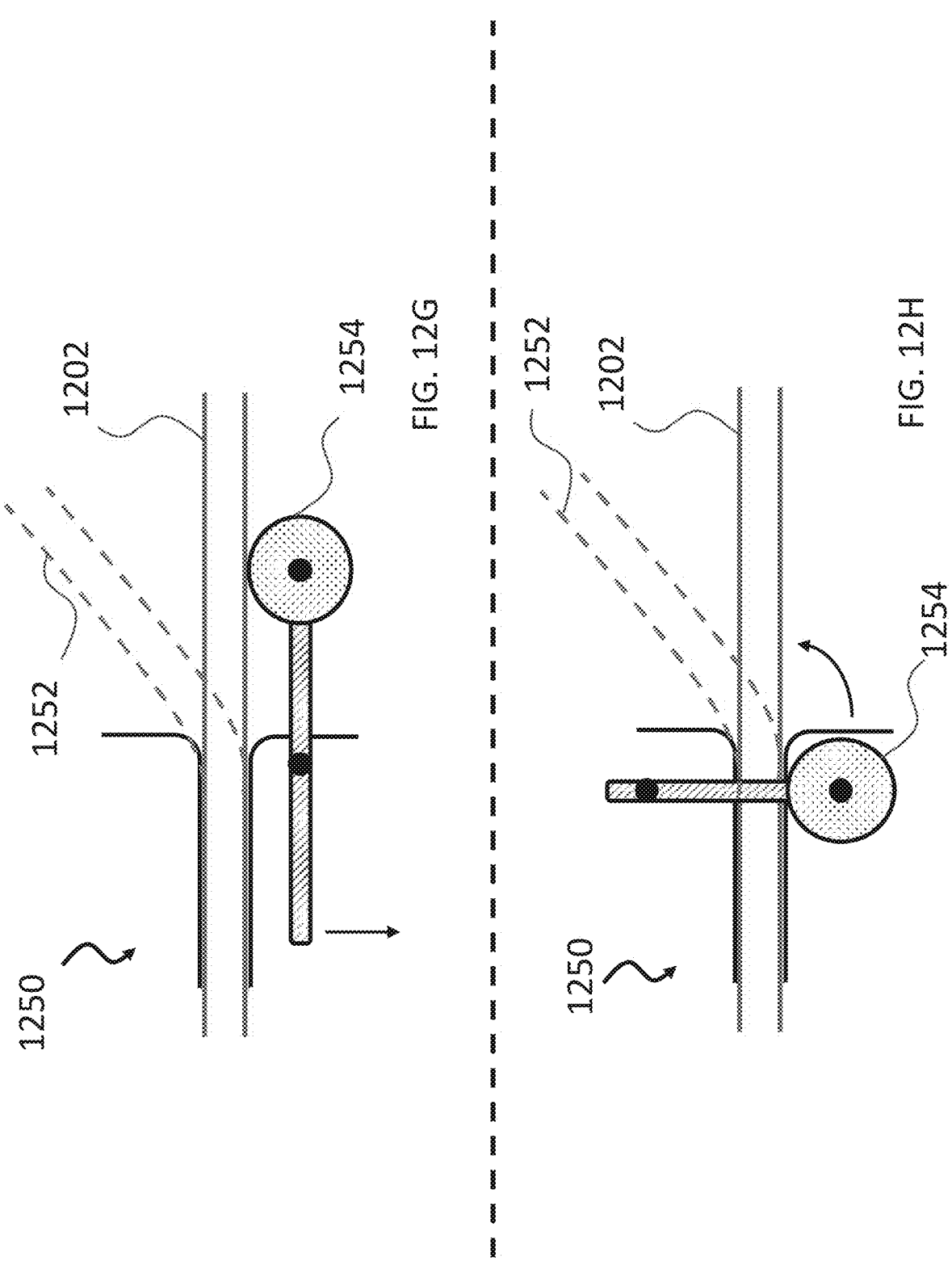

As shown in FIG. 12A, compression bending utilizes a fixed bending die 1242 and a clamp 1244 and 1246 on each end of the rod 1202. One of the clamps (e.g., 1246) is moved thereby forcing the rod 1202 to bend around the bending die 1242 (e.g., up to 180 degrees). In certain embodiments, a compression bending module can bend, twist, and lift an extrusion simultaneously to create unique shapes.

As shown in FIG. 12B, rotary draw bending utilizes a stationary or sliding pressure die 1220 and clamping block 1222 to hold a rod 1202 in place. A round bending die 1224 is rotated (e.g., up to 90 degrees) thereby bending the rod 1202 as it rotates. Using this method a rod 1202 can only be bent one radius at a time. The round bending die 1224 can be powered by hydraulics. A mandrel or other component can be incorporated to grip the rotary die 1224 such that creasing or misshaping of the rod 1202 is prevented. A wiper die 1226 is angled slightly off parallel from the workpiece to ensure the die's edge makes full contact with the tube just before the tangent point of the tube's inner radius.

As shown in FIG. 12C, ram bending uses a ram 1210 to force the rod 1202 on a pressure/bending dies 1212*a-b*. A ramming die 1210 pushes the rod 1202 onto the pressure dies 1212*a-b*, forcing the rod 1202 into the desired bended form.

A shown in FIG. 12D, three-roll bending pushes the rod 1202 around three different rolls 1232*a-c* placed in a triangular shape. The rolls 1232*a-c* are adjusted to form a precise angle, up to a 360-degree rotation, that can roll horizontally or vertically. The rod 1202 curves and bends as it is moved across the rollers 1232*a-c*. In certain embodiments, two of the rollers (e.g., 1232*a* and 1232*c*) are stationary and the third roller (e.g., 1232*b*) is a power roller that can be moved to change the bend radius.

FIGS. 12E through 12H illustrate additional bending modules. The rod 1202 is shown extending through the bending module 1250 prior to bending and the bent portion is shown after bending and labeled as 1252. The force dies 1254 are used to apply a force to the rod thereby bending the rod. The arrows show the direction of the forces that can be applied in the examples shown.

Figure 13:
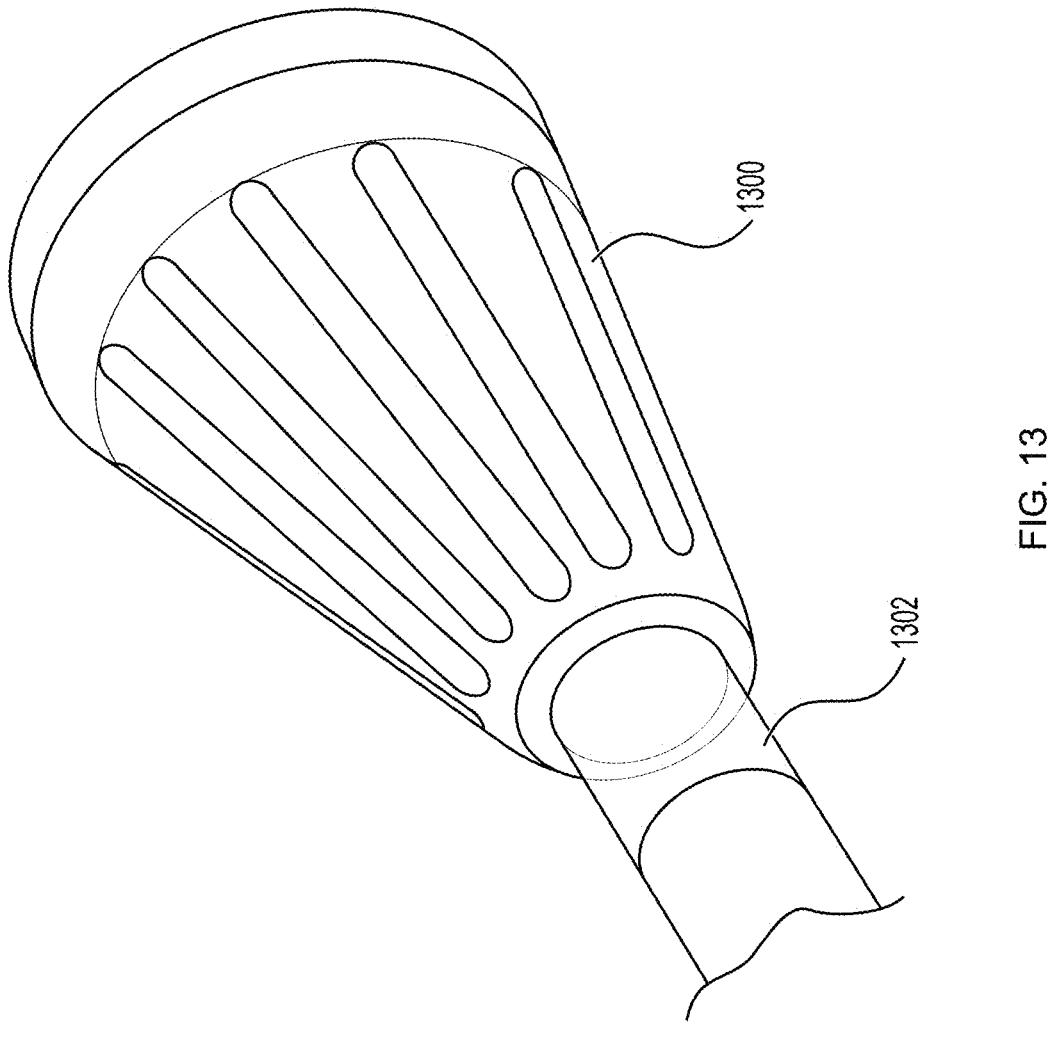
FIG. 13 is an illustration of an example rod fixation apparatus.
Figure 14C:
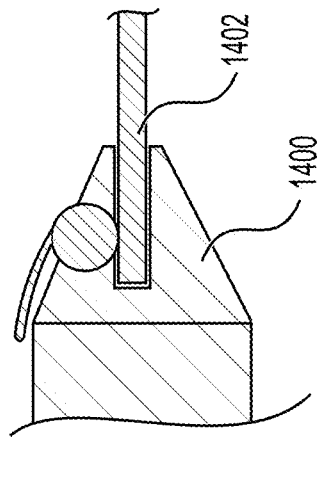
FIGS. 14A through 14D are illustrations of example fixation apparatuses.
Figure 14B:
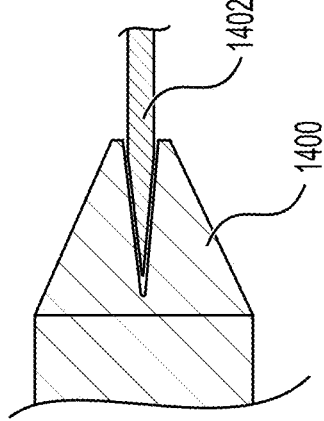
Figure 14D:
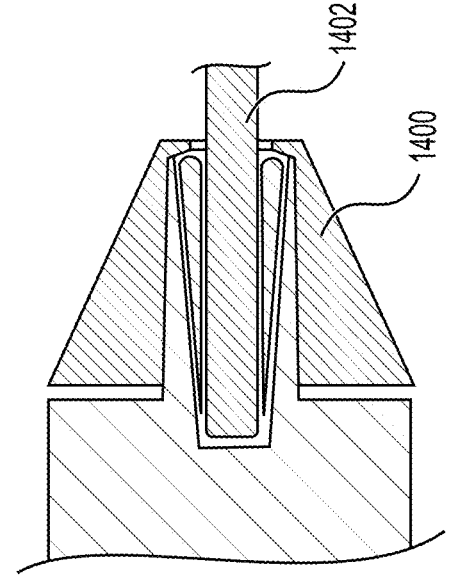
Figure 14A:
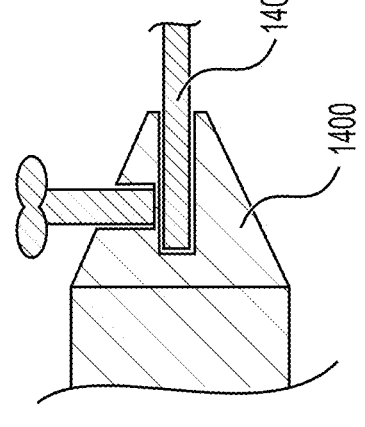

FIG. 13 is an illustration of an example rod fixation apparatus 1300. The rod fixation apparatus 1300, in certain embodiments, is used to securely hold the rod 1302. The rod fixation apparatus 1300 can be attached to the robot and integrated into the robot. In certain embodiments, the rod fixation apparatus 1300 is releasably secured to the mobile cart. In other embodiments, the rod fixation apparatus 1300 is releasably secured to the robotic arm. The arm can move the rod fixation apparatus 1300 and hence the rod 1302 secured therein to the appropriate positions such that the rod 1302 is bent in the desired configuration. This allows the bending device to be a simple device that simple bends a rod 1302. The determination of where and how to bend the rod 1302 can be done outside of the bending module itself and the robotic arm can position the rod 1302 and activate the bending module to produce the appropriately shaped rod 1302. FIGS. 14A though 14D illustrate example rod fixation apparatuses 1400 and specifically the device by which the rod fixation apparatus 1400 securely holds the rod 1402.

Figure 15:
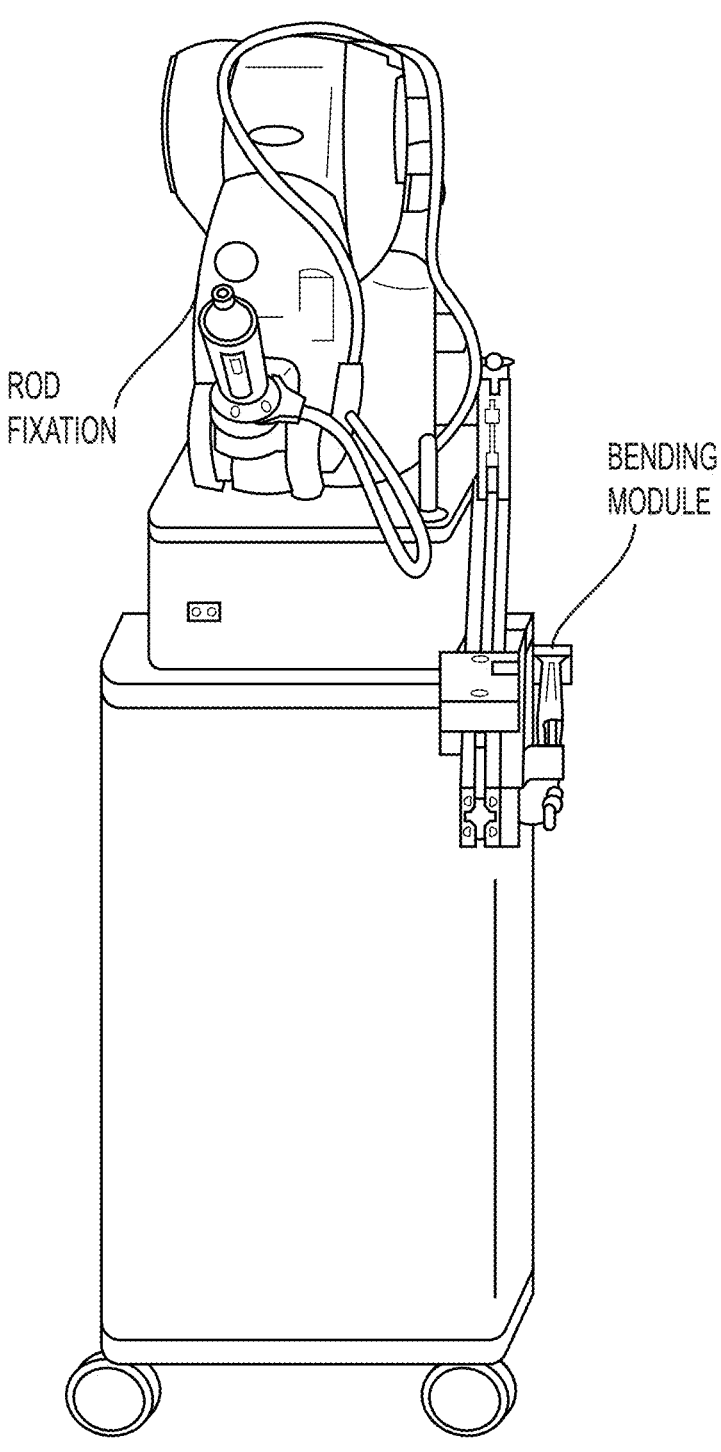
FIGS. 15 through 29 are photographs of an example robotic surgical system for bending rods.

FIG. 15 is a photograph of an example robotic surgical system with a bending module. As shown in this photograph, the rod fixation is attached to the robotic arm and the bending module is attached to the mobile car. Other orientation and/or connection points are available as well. For example, the rod fixation may be secured to the mobile cart and the bending module may be secured to the robotic arm.

Figure 16:
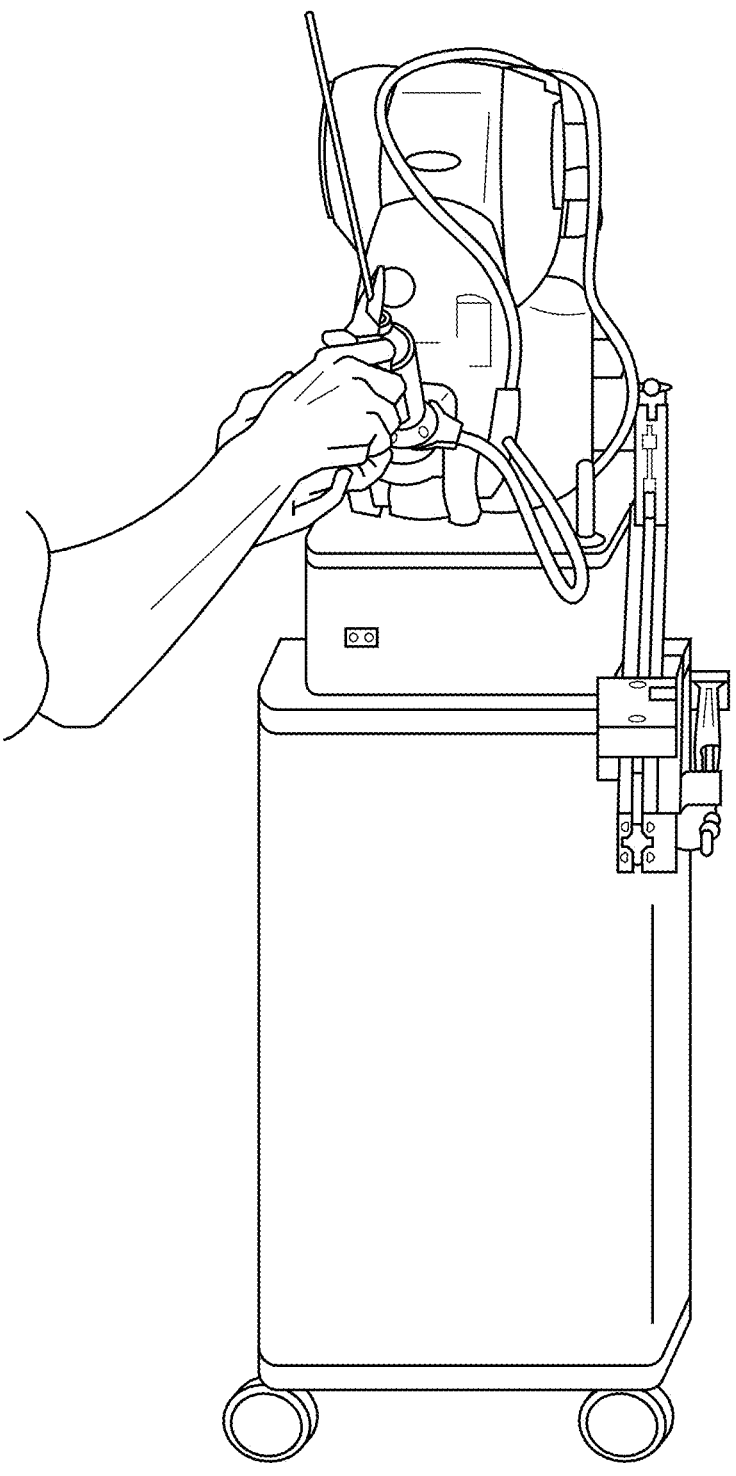

FIG. 16 is a photograph of a rod being inserted touch-free (e.g., without being touched by the user's hands) into the rod fixation on the robotic arm. In this example, the rod is inserted into the rod fixation using pliers.

Figure 17:
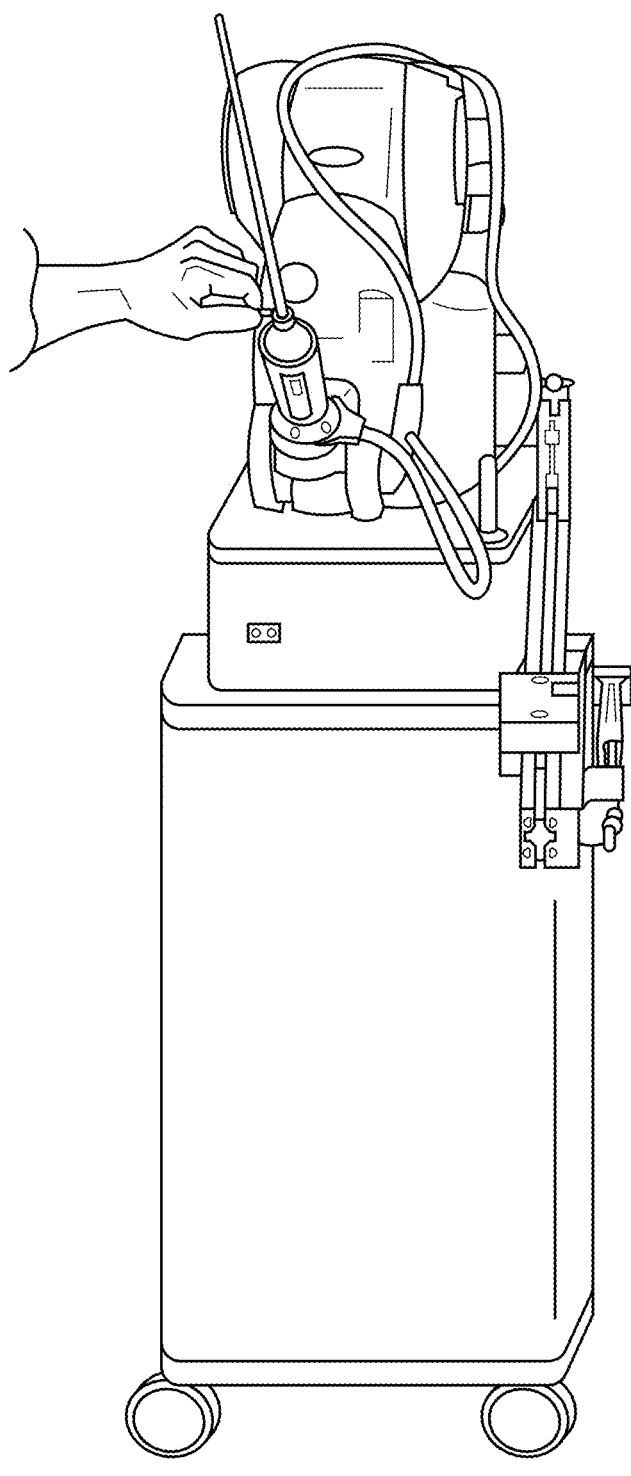

After inserting the rod into the rod fixation, the rod fixation is tightened to secure the rod therein as shown in FIG. 17. In this example, two bolts are tightened to secure the rod therein. In other examples more or less bolts are used or other grasping devices are used.

Figure 18:
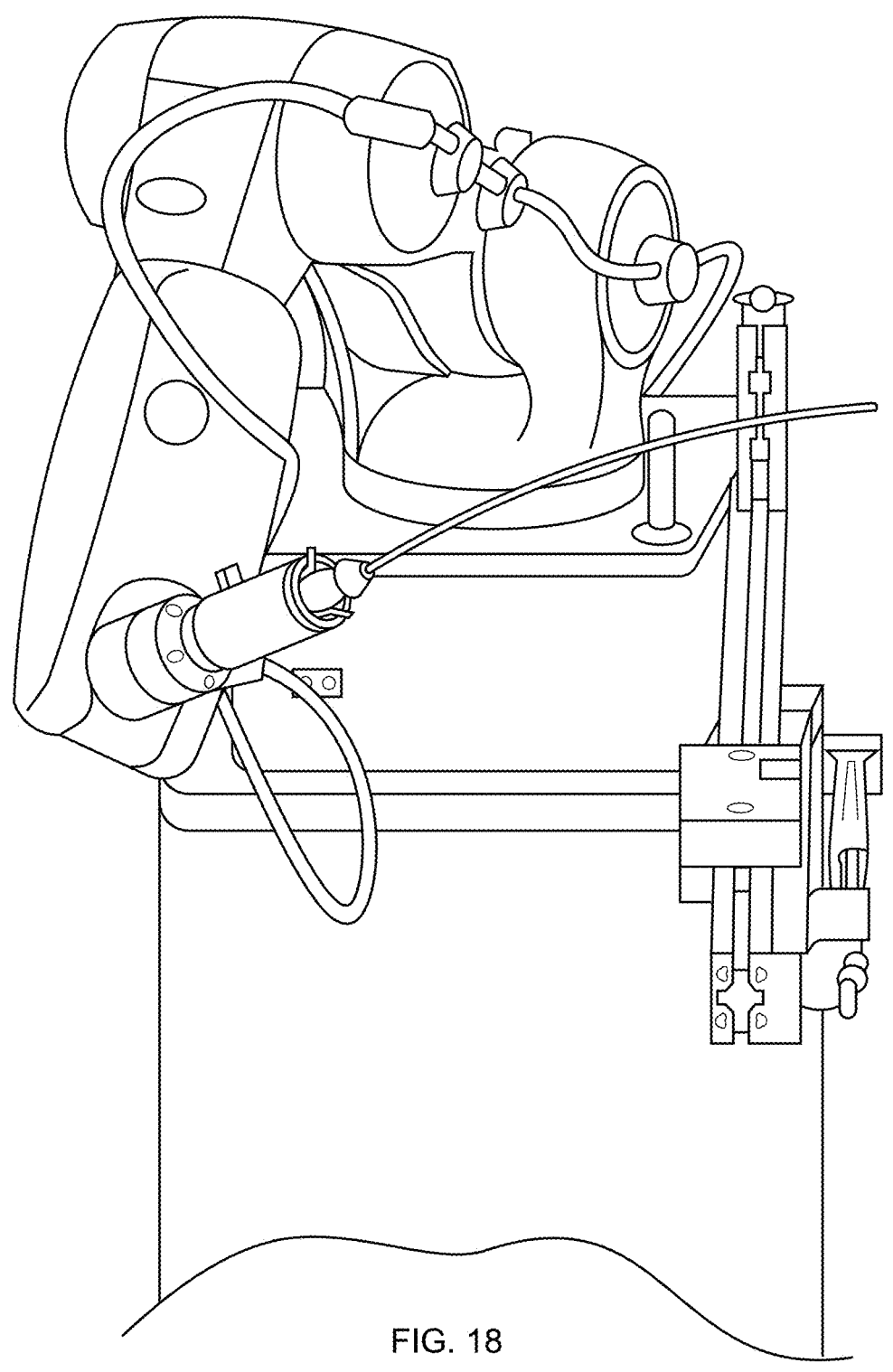
Figure 19:
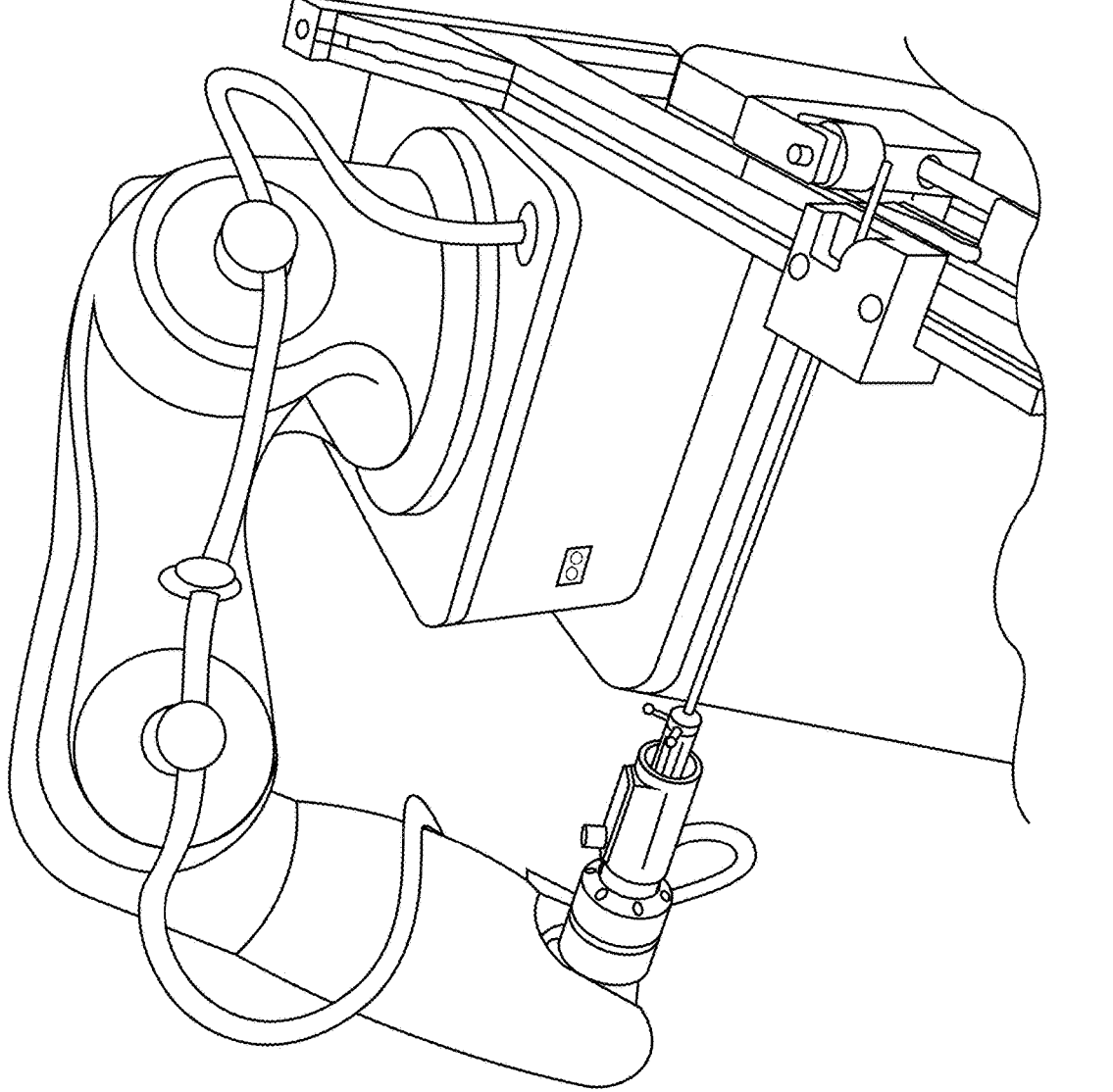
Figure 20:
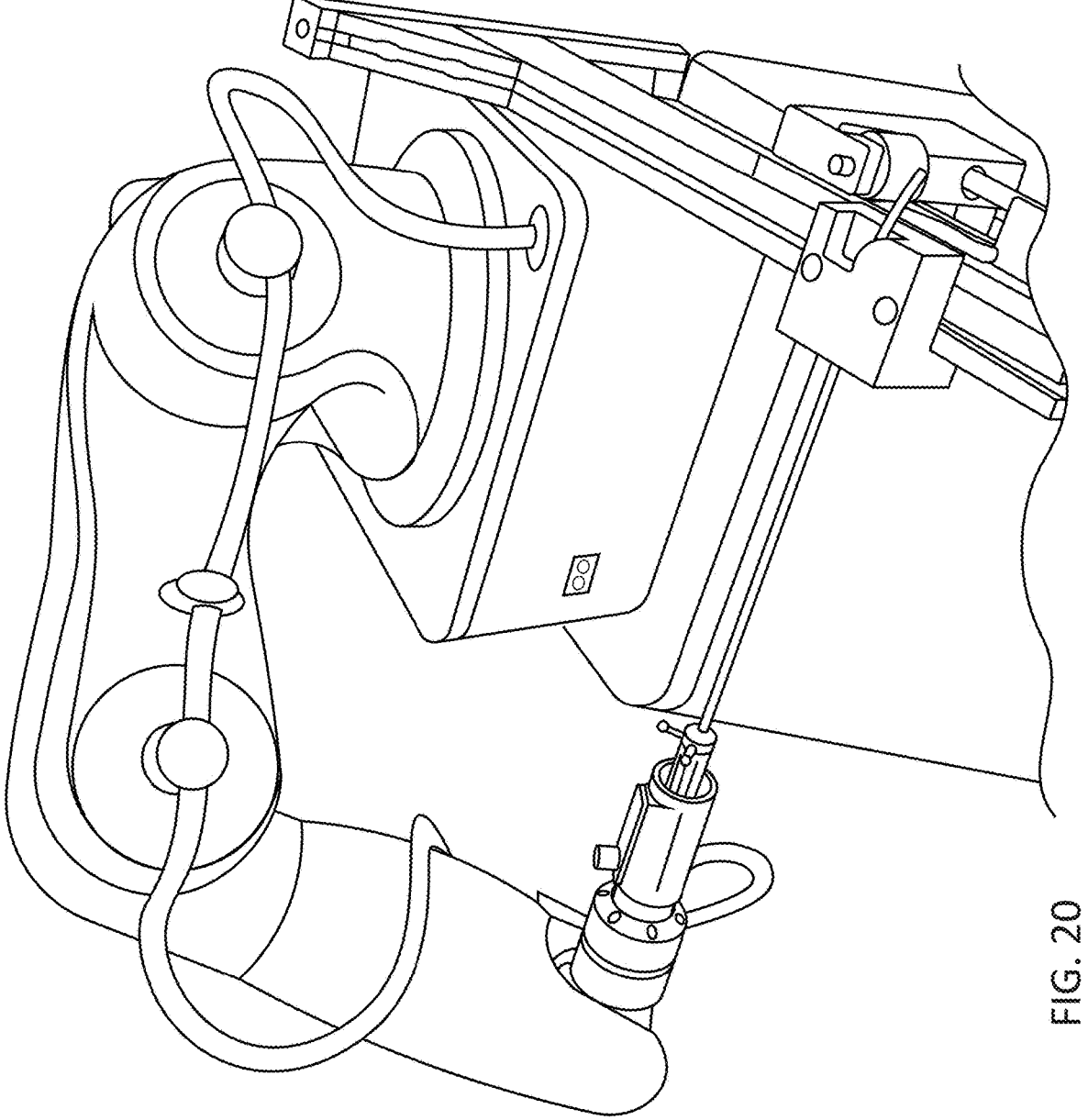
Figure 21:
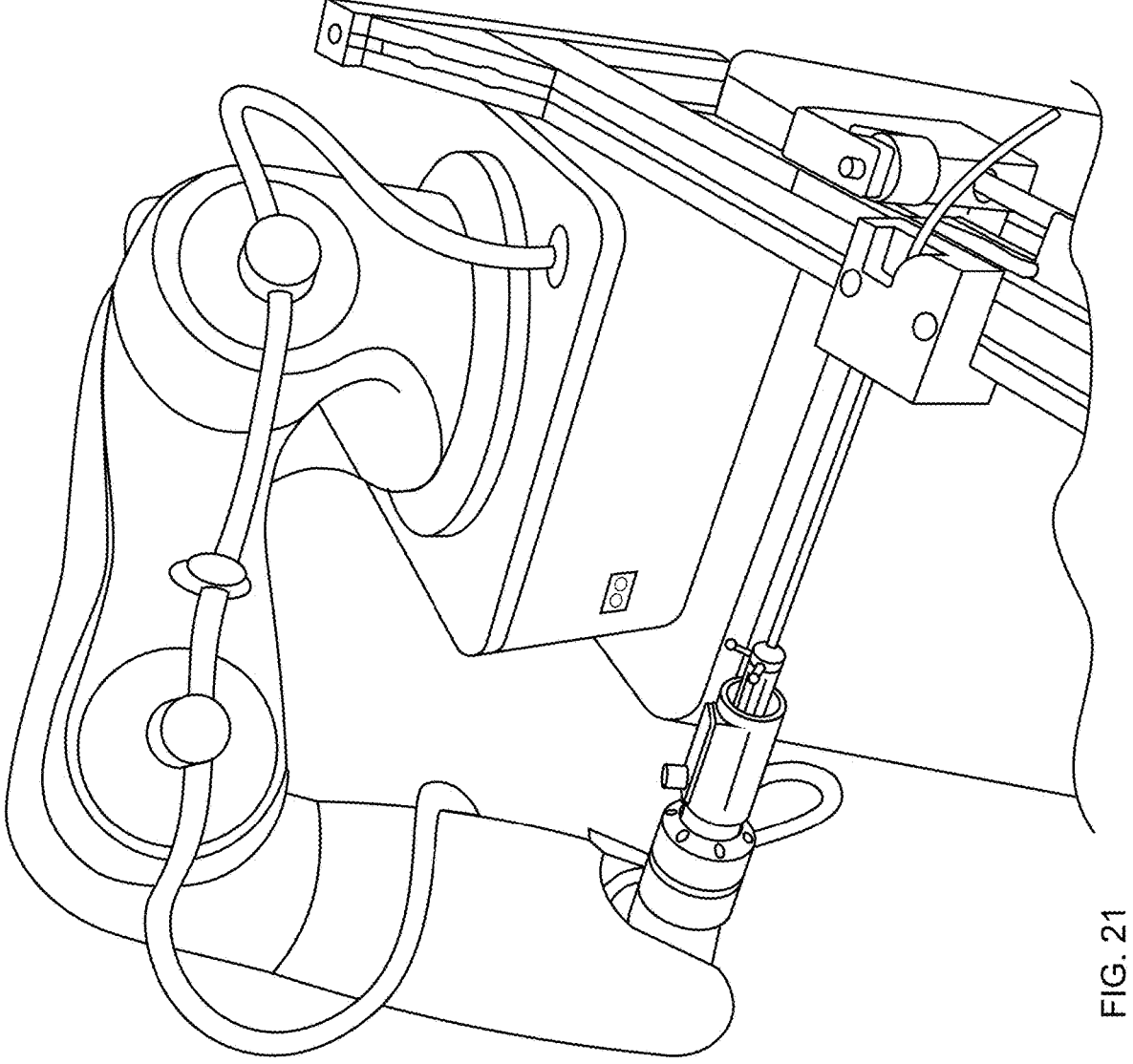
Figure 22:
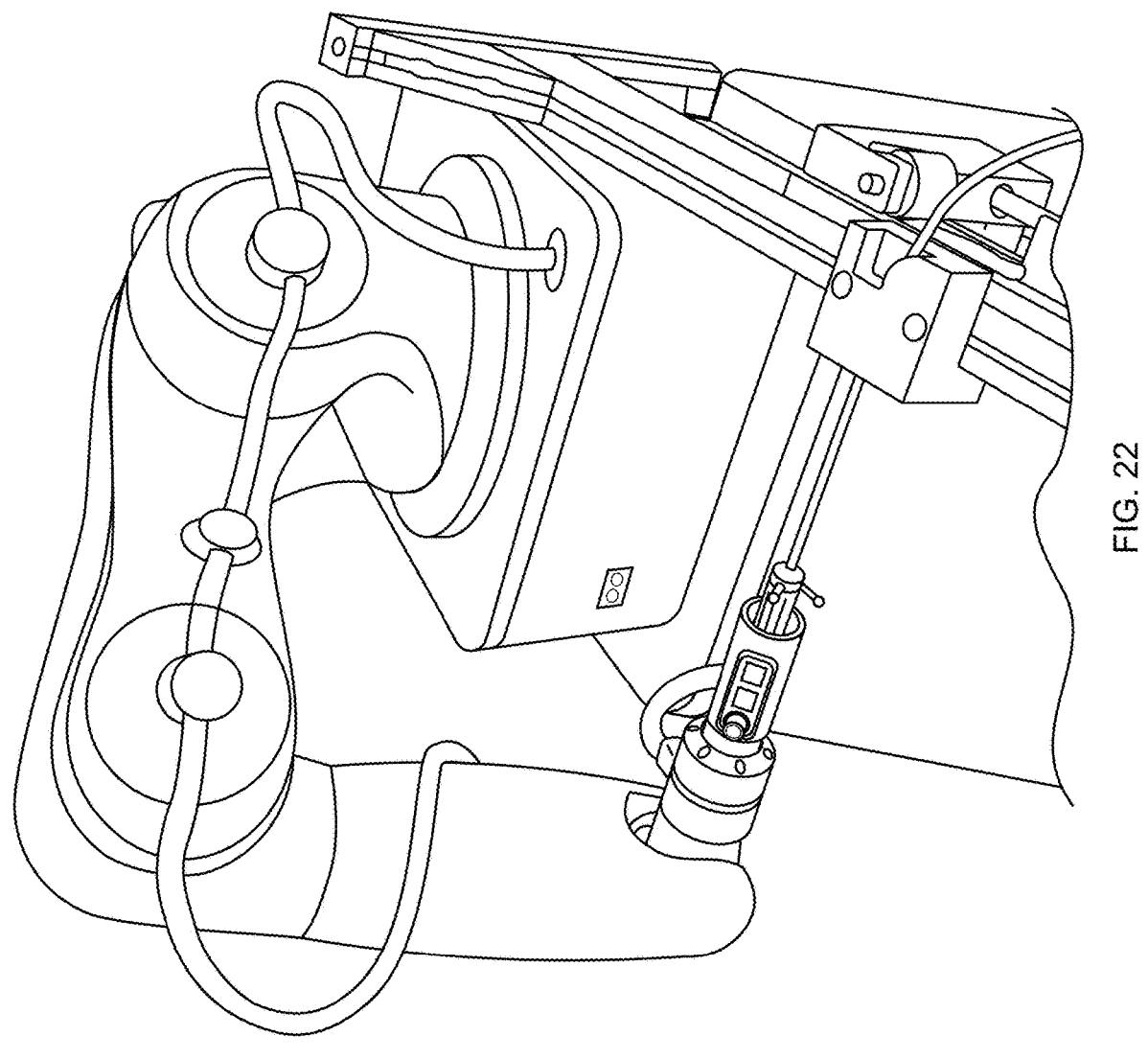
Figure 23:
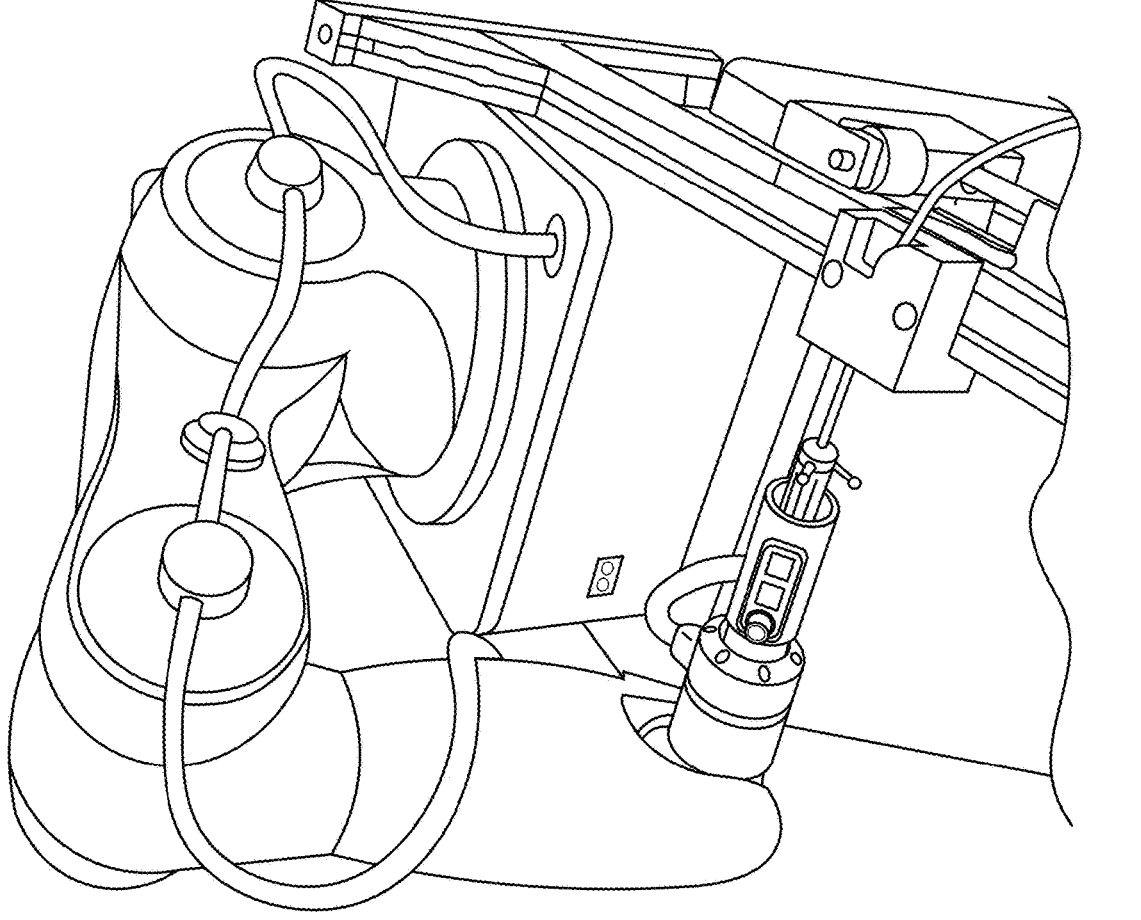

FIG. 18 is a photograph of the robotic surgical system moving the rod into the bending module so that it can be bent. In FIG. 19 the robotic surgical system has inserted the rod into the bending module and is being advanced to the appropriate location so it can be bent. FIG. 20 is a photograph of the bending module bending the rod. The robotic surgical system advances the rod, bends the rod, and repeats this process as shown in FIGS. 20 through 23 until the desired shaped rod is created. For example, the robotic arm advances the rod a determined distance into the bending module, the bending modules bends the rod, and then the robotic arm advances the rod a second determined distance. This continues until the desired shaped rod is create. Cutting of the rod by the bending module can be automatic.

Figure 24:
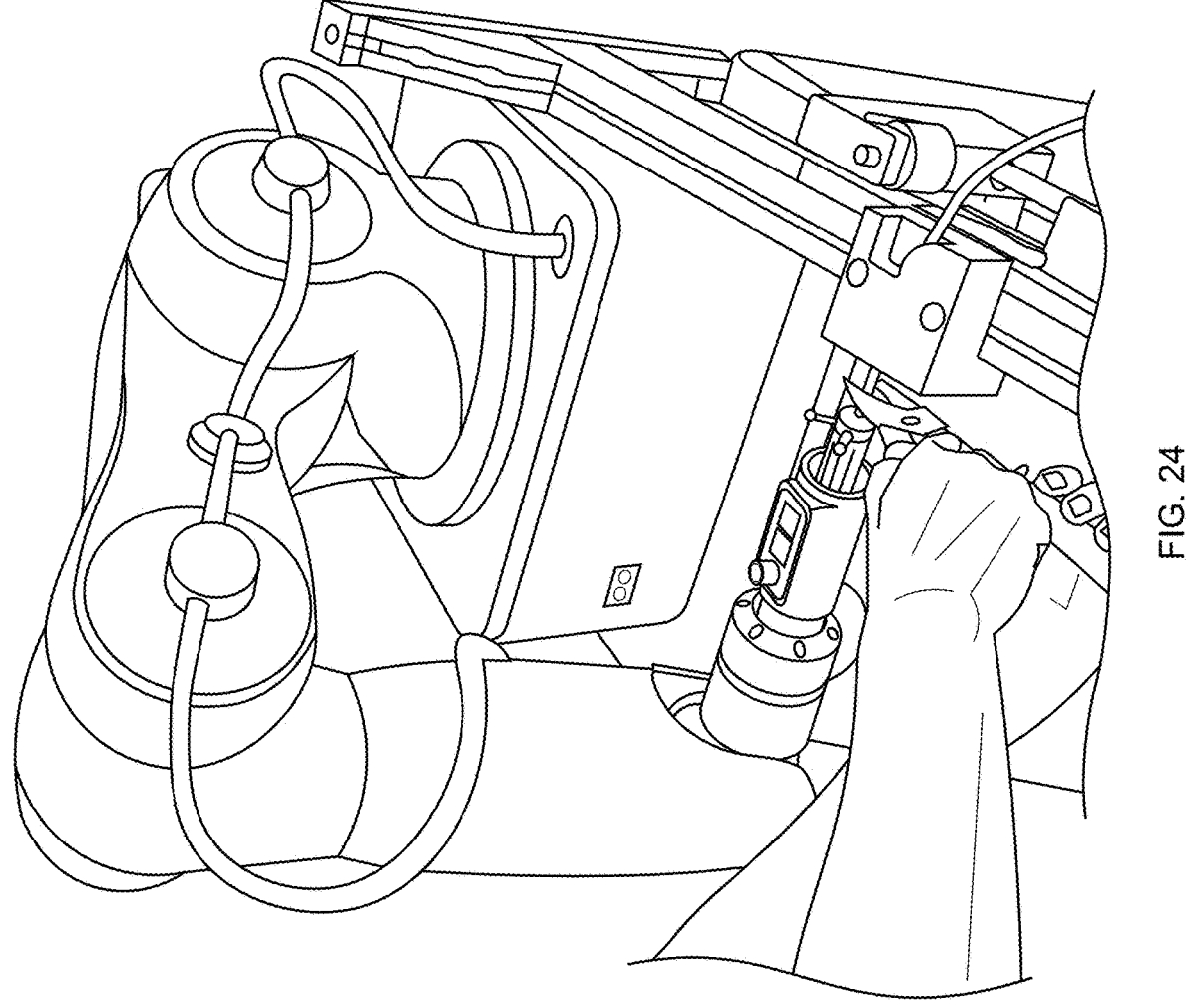
Figure 25:
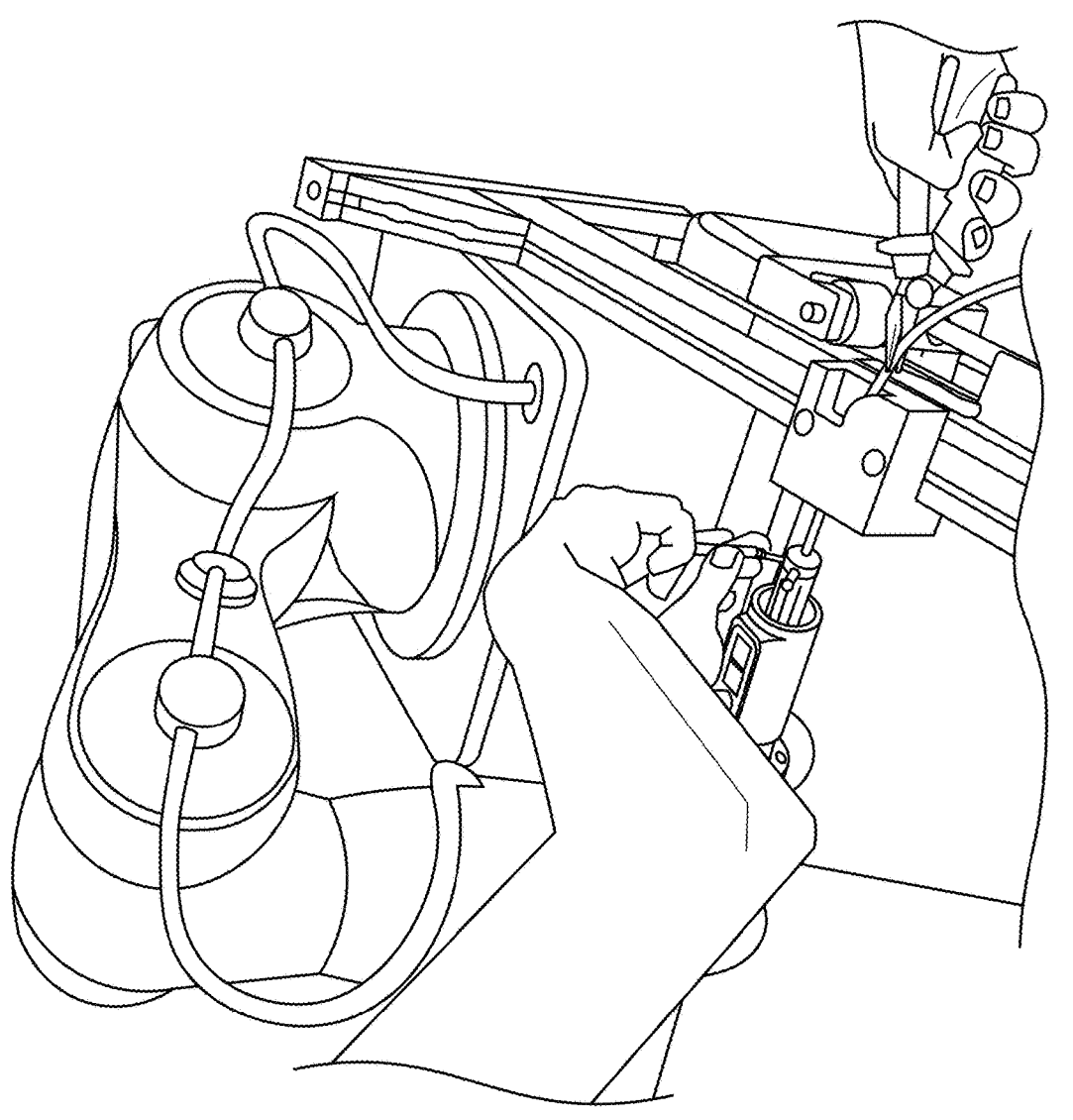
Figure 26:
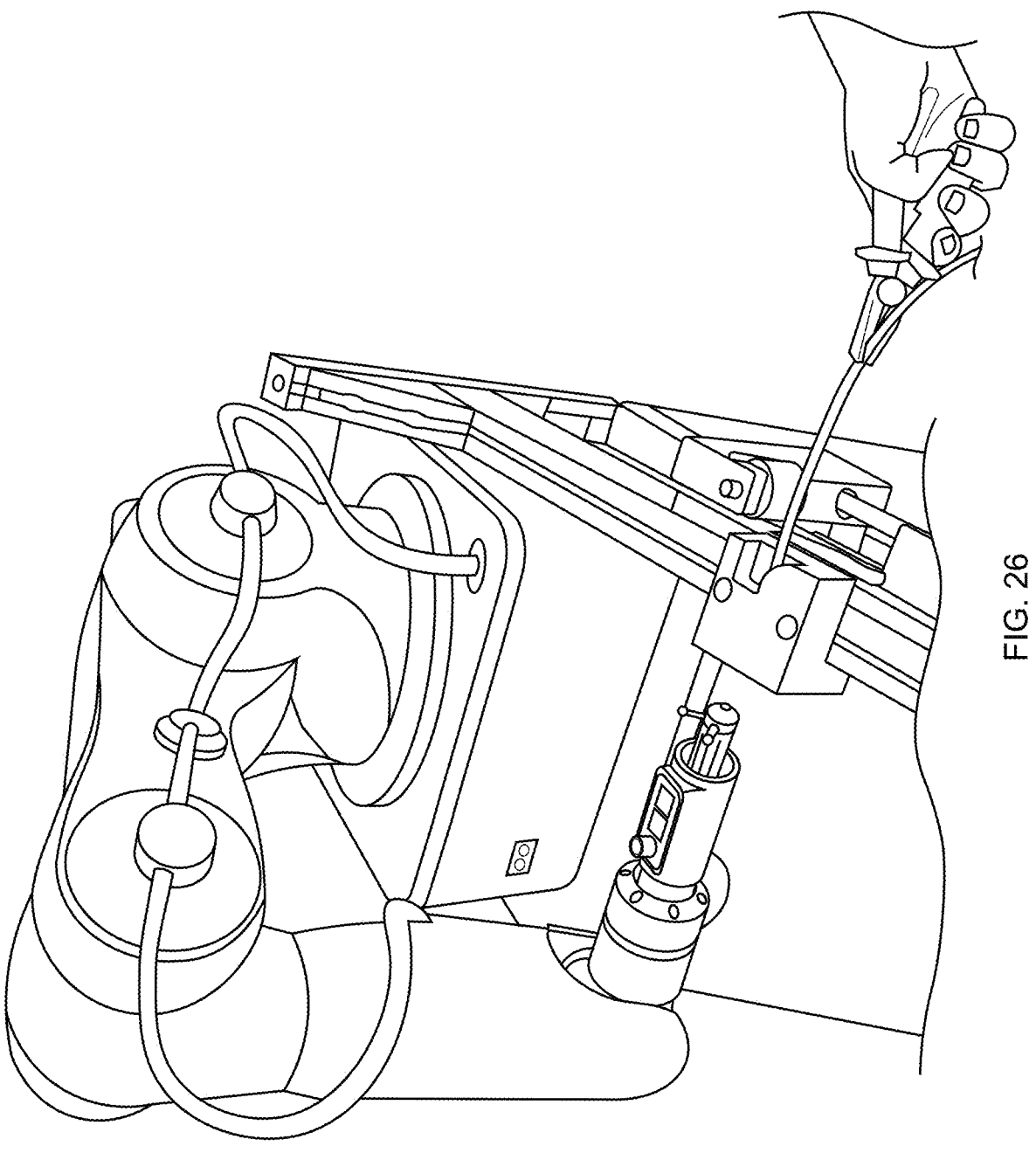

The rod is cut after the rod is bent into the desired shape. As shown in FIG. 24 the rod can be cut manually. In certain embodiments, a cutting device is integrated into the bending modules. In some implementations, instead of cutting the rod the rod fixation is loosened as shown in FIG. 25 such that the rod can be removed. After the rod is cut or the rod fixation is loosened, the rod can be removed as shown in FIG. 26.

Figure 27:
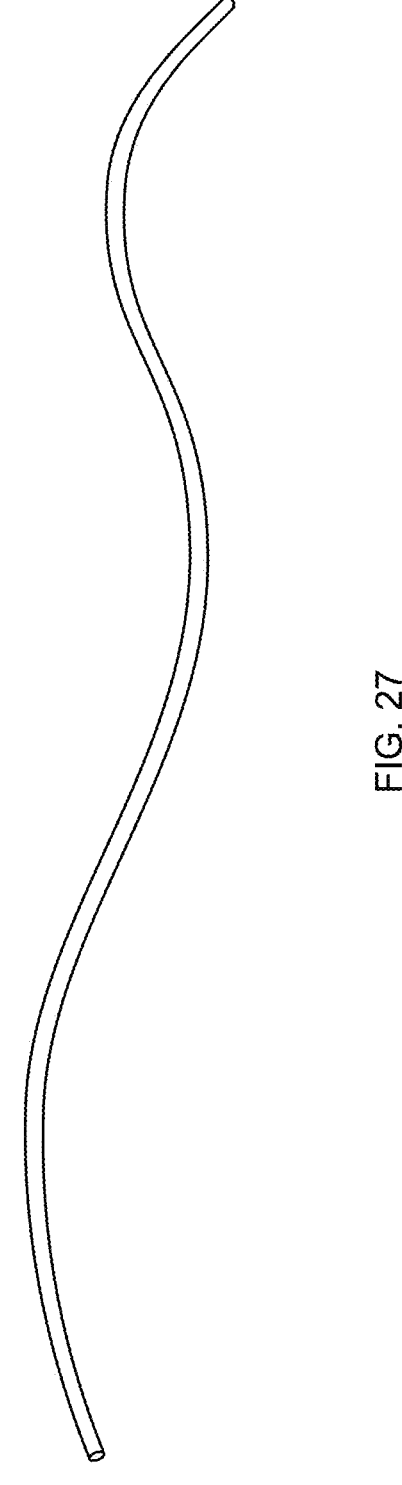
Figure 28:
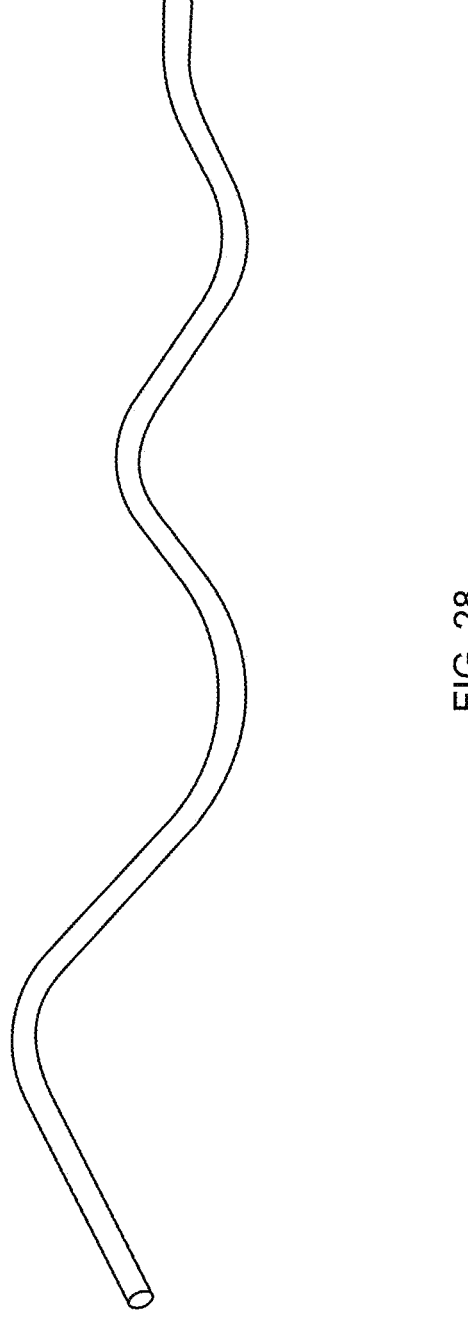
Figure 29:
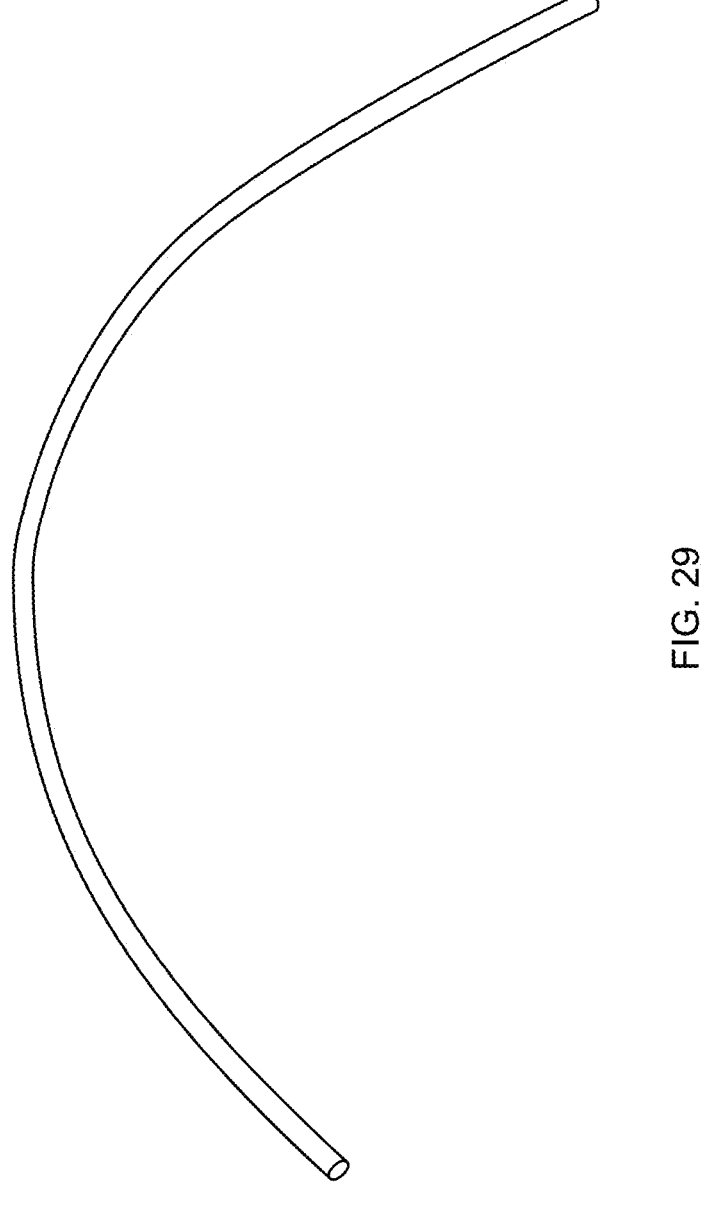

FIG. 27 is a photograph of a rod bent using the disclosed technology to provide smooth bends. FIG. 28 is an illustration of a rod bent using the disclosed technology. As shown in FIG. 28, the disclosed technology can be used to provide rods bent with a small bend radius even in tough materials such as CoCr+. FIG. 29 is an illustration of a rod bent using the disclosed technology to produce a rod with a three-dimensional curve.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A robotic surgical system for use in a spinal surgical procedure, the system comprising:
   a mobile cart having a top surface;
   a robot base having a top surface and a side surface, the side surface extending from the top surface of the mobile cart;

a bending apparatus located directly adjacent the top surface of the mobile cart and directly adjacent the side surface of the robot base;
a robotic arm extending from the top surface of the robot base and including an end-effector, the robot base and the robotic arm adapted to perform the spinal surgical procedure, wherein the robotic arm is configured to allow the end-effector to have at least three degrees of translational movement and at least three degrees of rotational movement;
an actuator for controlled movement of the robotic arm and positioning of the end effector; and
a processor and a non-transitory computer readable medium storing instructions thereon wherein the instructions, when executed, cause the processor to:
receive a pre-operatively planned curvature of a skeletal structure of a patient;
determine a position of each of two or more screws actually implanted in the patient during the surgical procedure using a pointing device and a navigation system that tracks the pointing device; and
intraoperatively determine a desired curvature of an implantable rod based at least in part on the pre-operatively planned curvature of the skeletal structure and the position of the two or more screws placed in the patient during the spinal surgical procedure,
wherein the end effector is adapted to securely receive the implantable rod, and wherein the instructions, when executed by the processor, cause the processor to:
position the end effector thereby positioning the rod relative to the bending; and
send signals to the bending apparatus that cause the bending apparatus to bend the rod.

2. The robotic surgical system of claim 1, wherein the end effector is adapted to securely receive the implantable rod, and wherein the instructions, when executed by the processor, cause the processor to:
   position the end effector and send signals to a bending apparatus thereby causing the bending apparatus to bend the rod, thereby creating a shaped rod.

3. The robotic surgical system of 1, further comprising a rod fixation apparatus for grasping a rod.

4. The robotic surgical system of claim 3, wherein the rod fixation apparatus is arranged to be held by the end effector.

5. The robotic surgical system of 1, further comprising:
   the bending apparatus for bending a rod, the bending apparatus comprising:
   a force die;
   a bend die;
   a force transfer device that transfers energy from an actuator to the force die thereby causing a rod positioned between the force die and the bend die to bend around the bend die; and
   a fixation apparatus for releasably securing the bending apparatus to the robotic surgical system.

6. A robotic surgical system for performing a spinal surgical procedures, the system comprising:
   a mobile cart having a top surface;
   a robot base having a top surface and a side surface, the side surface extending from the top surface of the mobile cart;
   a bending apparatus for bending a rod, the bending apparatus located directly adjacent the top surface of the mobile cart and directly adjacent the side surface of the robot base;
   a robotic arm extending from the top surface of the robot base and including an end-effector, the robot base and the robotic arm adapted to perform the spinal surgical procedure and for bending a rod during the surgical procedure, wherein the robotic arm is configured to allow the end-effector to have at least three degrees of translational movement and at least three degrees of rotational movement;

a rod fixation apparatus adapted to be attached to the end effector and configured for grasping the rod;

an actuator for controlled movement of the robotic arm and positioning of the end effector; and a processor and a non-transitory computer readable medium storing instructions thereon wherein the instructions, when executed, cause the processor to:

control the robotic arm to position the grasped rod within the bending apparatus;

intraoperatively coordinate the bending of the grasped rod to produce a shaped rod based at least in part on a desired curvature of a skeletal structure and the position of each of two or more implanted screws in the patient during the spinal surgical procedure.

7. The robotic surgical system of claim 6, wherein the instructions, when executed by the processor, cause the processor to:

receive a desired curvature of a skeletal structure of a patient;

determine a position of each the two or more screws in the patient during the surgical procedure; and intraoperatively determine the desired curvature of an implantable rod based at least in part on the desired curvature of the skeletal structure and the position of the two or more screws placed in the patient during the surgical procedure.

8. The robotic surgical system of claim 7, wherein the instructions, when executed by the processor, cause the processor to:

position the end effector thereby positioning the grasped rod relative to the bending apparatus; and send signals to the bending apparatus that cause the bending apparatus to bend the rod as the end effector positions the grasped rod within the bending apparatus.

9. The robotic surgical system of claim 7, wherein the instructions, when executed by the processor, cause the processor to:

position the end effector and send signals to the bending apparatus thereby causing the bending apparatus to bend the rod, thereby creating a shaped rod.

10. The robotic surgical system of claim 7, wherein the desired curvature of the skeletal structure is determined pre-operatively.

11. The robotic surgical system of claim 7, wherein the position of each of the two or more screws is the patient is determined intra-operatively.

12. The robotic surgical system of claim 7, wherein the position of each of the two or more screws in the patient is determined using a navigation system.

13. The robotic surgical system of claim 12, wherein the position of each of the two or more screws in the patient is determined using a point device with the navigation system to identify the locations of the screws during the surgical procedure.

14. The robotic surgical system of claim 13, wherein the rod fixation apparatus is arranged to be held by the end effector.

15. The robotic surgical system of 12, wherein the bending apparatus comprises:

a force die;

a bend die; and a force transfer device that transfers energy from an actuator to the force die thereby causing a rod positioned between the force die and the bend die to bend around the bend die.

* * * * *